(12) United States Patent
Gross et al.

(10) Patent No.: US 7,306,952 B2
(45) Date of Patent: Dec. 11, 2007

(54) MOLECULAR FINGERPRINTING OF TRIGLYCERIDES IN BIOLOGICAL SAMPLES BY ELECTROSPRAY IONIZATION TANDEM MASS SPECTROMETRY

(75) Inventors: Richard W. Gross, Chesterfield, MO (US); Xianlin Han, Clayton, MO (US)

(73) Assignee: Washington University in St. Louis, St. Louis ( * ) Notice: Subject to any disclaimer, the term of this patent is extended or adjusted under 35 U.S.C. 154(b) by 288 days.

(21) Appl. No.: 10/606,601

(22) Filed: Jun. 26, 2003

(65) Prior Publication Data

US 2004/0063118 A1  Apr. 1, 2004

Related U.S. Application Data

(60) Provisional application No. 60/391,711, filed on Jun. 26, 2002.

(51) Int. Cl.
G01N 24/00 (2006.01)
G01N 33/22 (2006.01)
(52) U.S. Cl. .......................... 436/173; 436/71
(58) Field of Classification Search .................. 436/71
See application file for complete search history.

(56) References Cited

OTHER PUBLICATIONS

Han et al. "Electrospray ionization mass spectroscopic analysis of human erythrocyte plasma membrane phospholipids," Proc. Natl. Acad. Sci, vol. 91, 10635-10639, (1994).*

Brügger et al. "Quantitative analysis of biological membrane lipids at the low picomole level by nano-electrospray ionization tandem mass spectrometry",Proc. Natl. Acad. Sci.,USA, Mar. 1997, vo. 94, pp. 2339-2344.*

Koivusalo et al. "Quantitative determination of phospholipid compositions by ESI-MS: effects of acyl chain length, unsaturation, and lipid concentration on instrument response", J. Lipid. Res., Apr. 2001, v. 42, pp. 663-672.*

Han, X. and Gross, R.W. "Quantitative Analysis and Molecular Species Fingerprinting of Triacylglyceride Molecular Species Directly from Lipid Extracts of Biological Sample by Electrospray Ionization Tandem Mass Spectrometry", Anal. Biochem., 2001, v. 295, pp. 88-100 (published on-line Jun. 27, 2001).*

Houjou et al. "Rapid and selective identification of molecular species in phosphatidylcholine and sphingomyelin by conditional neutral loss scanning and MS3", Rapid Comm. Mass Spectrom., 2004, v. 18, pp. 3123-3130.*

\* cited by examiner

*Primary Examiner*—Yelena G. Gakh
(74) *Attorney, Agent, or Firm*—Armstrong Teasdale LLP

(57) ABSTRACT

A method for determination of at least one of the triglyceride molecular species in a biological sample comprising the subjecting sample to lipid extraction to obtain a lipid extract and subjecting the resulting lipid extract to 2D electrospray ionization tandem mass spectrometry (ESI/MS/MS) with neutral loss scanning of all naturally occurring aliphatic chains and contour analysis of 2D intercept peaks. A method for determination of tricylglyceride content and/or TG molecular species directly from a lipid extract of a biological sample comprising subjecting said lipid extract to electrospray ionization tandem mass spectrometry.

17 Claims, 5 Drawing Sheets

MOLECULAR FINGERPRINTING OF TRIGLYCERIDES IN BIOLOGICAL SAMPLES BY ELECTROSPRAY IONIZATION TANDEM MASS SPECTROMETRY

CROSS REFERENCE TO RELATED APPLICATION

This application claims the priority of U.S. provisional patent application 60/391,711 filed Jun. 26, 2002 which is hereby incorporated by reference in its entirety.

STATEMENT REGARDING FEDERALLY SPONSORED RESEARCH & DEVELOPMENT

This work was supported by grants from NIH including grants W/H P01 HL57278/JDFI 996003, R02HL41250 and R01 AA11094. The government has certain rights in the invention.

FIELD OF THE INVENTION

This invention relates generally to a method of analysis for triglycerides in a biological sample. More particularly this invention relates to a method for analysis and individual molecular species quantification of triglycerides in a biological sample.

This invention also relates to the fingerprinting detection, diagnosis and treatment of triglycerides in blood, vessels, atheroma, liver, stool and other body tissues as well as biopsies of body organs such as a liver or a muscle biopsy.

This invention also relates to a method of determining the risk to an individual of TG molecular species as an independent factor in the development of coronary artery disease, stroke, atherosclerosis and obesity as well as to target agents to selectively modify triglyceride (hereinafter "TG") molecular species.

This invention also relates to the fingerprinting, detection, diagnosis and treatment of triglycerides in blood, liver, stool, sputum and other body tissues as well as biopsies of body organs such as a liver or a muscle biopsy. Also this invention relates to a method of screening drugs to determine those lipid modulating drugs which are efficacious in clinical trials and to monitor the response of patients to a specific drug therapy to determine the best or optimum drug for each patient.

BACKGROUND OF THE INVENTION

Triglycerides comprise linear combinations of aliphatic chains covalently attached to a glycerol backbone. Triglycerides serve as vital sources of cellular energy and caloric potential in living organisms. Recent work has provided unambiguous evidence of the importance of total triglycerides as a lipid class to the development of heart disease, stroke, obesity and diabetes in humans all of which are life taking diseases which take a staggering toll of human lives each year. Additionally, such afflictions destroy or significantly reduce the quality of life even if not immediately fatal.

Triglycerides (TG) includes molecules of glycerol esterified with three fatty acids. TG have a glycerol backbone structure while the associated fatty acids are predominately unsaturated. Dihydroxyacetone phosphate (DHAP) or glycerophosphate produced during glycolysis is the precursor for triacylglycerol synthesis (Triacylglycerides are triglycerides) in mammalian cells including adipocytes and hepatocytes.

In mammals, complex and diverse mechanisms have evolved to regulate the TG content in serum, the delivery of fatty acids derived from serum TG molecular species to cells (e.g., lipoprotein lipase and fatty acid transport protein), and the intracellular storage of fatty acids by esterification to a glycerol backbone for subsequent storage as TG molecular species. It is highly desired to be able to readily determine the identity of TG molecular species along with their respective quantity present in biological samples including living mammalian and plant samples. In many such areas of research and medical therapy it is desired and necessary to analyze large and increasing numbers of biological samples in an enhanced fashion such as those samples comprising TG molecular species.

For at least the aforegoing reasons biological analytical methods which readily and directly identify and quantify TG molecular species in biological samples will be an integral and vital part of research which produces discoveries of benefit to mankind in the biochemistry of plants and animals dealing with coronary artery disease, stroke, atherosclerosis and obesity. Accordingly an enhanced analysis of such biological samples is needed which provides a TG molecular species profile.

The TG molecular species profile reflects the nutritional and metabolic history of each cell as well as its anticipated energy storage requirements. Alterations in TG molecular species synthesis and catabolism have been demonstrated to play prominent roles in obesity, atherosclerosis, insulin release from pancreatic β cells, and alcohol-induced hepatic dysfunction (1-7). Moreover, recent studies have identified the importance of alterations in intracellular triglycerides as a potential mediator of diabetic cardiomyopathy (5,8).

Although some studies have measured total TG molecular species content in multiple different disease states, a paucity of information on TG molecular species changes during pathophysiological alterations is available. The first detailed molecular species analyses of TG in diabetic rat myocardium demonstrated a dramatic alteration in TG molecular species composition without substantial changes in TG mass (8). Accordingly, it seems likely that changes in TG molecular species composition also contributes to the pathophysiological sequelae of other disease states.

Previous attempts at direct TG quantitation by positive-ion electrospray ionization mass spectrometry (ESI/MS) were undesirably confounded by the presence of overlapping peaks from choline glycerophospholipids requiring chromatographic separation of lipid extracts prior to ESI/MS analyses. Thus it is highly desired to have an enhanced method and system for determining TG content in various living mammalian and plant cellular systems which obviates the chromatographic separation process requirement. Moreover, isobaric molecular species present in all biological tissues prevent determination of individual molecular species of triglycerides from molecular weight determinations alone.

BRIEF DESCRIPTION OF THE INVENTION

In a first embodiment, a method for the determination of TG individual (i.e. separate) molecular species composition of matter in a biological sample comprises subjecting the biological sample to lipid extraction to obtain a lipid extract and subjecting the lipid extract to electrospray ionization tandem mass spectrometry (ESI/MS/MS) providing TG molecular species composition as a useful output determination.

In an aspect, a method for the determination of TG individual (i.e. separate) molecular species composition of matter directly from a lipid extract of a biological sample comprises subjecting the lipid extract to electrospray ionization tandem mass spectrometry using neutral loss scanning and two dimensional density contour analysis.

In an aspect, neutral loss scanning is used with electrospray ionization tandem mass spectrometry.

In an aspect, TG content is obtained by summing and obtaining the total of the TG individual (i.e. separate) molecular species.

In an aspect, the inventive concept comprises analyzing a biological sample using electrospray ionization tandem mass spectrometry (ESI/MS/MS) and performing a two dimensional analysis with cross peak contour analysis on the output of the ESI/MS/MS to provide a fingerprint triglyceride individual (i.e. separate) molecular species.

In an aspect, TG content is obtained by summing and obtaining the total of the TG individual (i.e. separate) molecular species.

In an aspect, a diagnostic kit for the determination of triglyceride molecular species in a biological sample comprises components suitable for carrying out at least one of a method for the determination of triglyceride (TG) content and/or molecular species composition of matter in a mammalian and plant biological sample comprises subjecting said biological sample to lipid extraction to obtain a lipid extract and subjecting the lipid extract to electrospray ionization tandem mass spectrometry (ESI/MS/MS) using neutral loss scanning providing as output the TG content and a method for the determination of triglyceride content and/or molecular species directly from a lipid extract of a biological sample comprising subjecting the lipid extract to electrospray ionization tandem mass spectrometry using neutral loss scanning.

In an aspect, the kit is housed in a container.

In an aspect, a method for assessing a risk to each (individual) subject (or group of individuals) based on TG molecular species as an independent factor in the development of at least one condition in that individual for a medical condition selected from coronary artery disease, stroke, atherosclerosis and obesity which comprises analyzing a biological sample of an individual for TG molecular species determination, administering of a drug to the individual, analyzing a corresponding biological sample of said administered to treated individual for TG molecular species determination, comparing the TG molecular species determination after drug administration with the TG molecular species determination prior to drug administration and determining a risk therefrom associated with that individual. In an aspect, the comparison of the TG molecular species determination of the biological samples is predictive of the likelihood of development of the condition for that subject and its prevention by tailored drug therapy.

In an aspect, the comparison is indicative of a predisposition of an individual to develop a condition. In an aspect, the condition is a desirable condition. In an aspect the condition is an undesirable condition. In an aspect, the condition is a medical condition which is desirable or undesirable. In an aspect, a desirable medical condition is a lowered triglyceride content of a human's blood.

In an aspect, a method for determining an agent which selectively targets triglyceride molecular species (e.g., saturated triglycerides) comprises analyzing a biological sample of at least one individual for TG molecular species determination, administering a therapeutic amount of a drug to the individual, analyzing a biological sample of said administered individual for TG molecular species determination, comparing the TG molecular species determination after said administration with the TG molecular species determination prior to the drug administration and determining an effect if any on the individual of the drug administration. In an aspect, the comparison of the TG molecular species determination of the biological samples is indicative of development of the condition for that (treated) individual.

In an aspect, a method of identifying a candidate lipid modulating drug having lipid modulating drug efficacy comprises selecting a biological sample to be taken, analyzing a biological sample of at least one individual for TG molecular species determination, administering of a candidate lipid modulating drug to the individual, analyzing a biological sample of treated individual, comparing the TG molecular species determination after said administration with the TG molecular species determination prior to the drug administration and determining an effect on the individual of the drug administration. In an aspect, the comparison of TG analysis is indicative of the efficacy a lipid modulating capacity of an administered drug.

In an aspect, a method to diagnose and determine the response of patients to tailored drug therapy comprises analyzing a biological sample taken of at least one individual for TG molecular species determination, administering a drug to the patient (hereinafter treated patient), analyzing a biological sample taken of the treated patient for TG molecular species determination, comparing the TG molecular species determination after the administration with the TG molecular species determination prior to the drug administration and determining an effect on the individual of the drug administration. In an aspect, the comparison of TG molecular species determination (analysis) is indicative of the efficacy a tailored drug therapy. In several aspects, the effect comprises a positive effect, a negative effect and no effect.

In an aspect, a method of screening candidate chemicals for lipid modulating potential in a subject comprises analyzing a biological sample of at least one individual for TG molecular species determination, administering a therapeutic amount of a drug to that biological subject, analyzing a biological sample taken from the administered to subject for TG molecular species determination, comparing the TG molecular species determination after said administration with the TG molecular species determination prior to the drug administration and determining an effect if any on the subject of the drug administration. In an aspect, the comparison of TG analysis is indicative of the efficacy a candidate chemical having a lipid modulating potential.

In an aspect, a method of treating a subject comprises analyzing a biological sample taken of that subject for TG molecular species determination by a method comprising ESI/MS/MS with neutral loss scanning and two dimensional contour analysis. In an aspect, the subject is human.

In an another aspect, a medical treatment comprises analyzing a biological sample taken of a subject for TG molecular analysis by ESI/MS/MS. In an aspect the medical treatment is for a human.

In an aspect, a method of customizing drug therapy for a subject comprises analyzing a biological sample taken of the subject for TG molecular species determination by ESI/MS/MS and adjusting the subject's drug therapy based on the results of the TG molecular species determination. In an aspect, the subject is human.

In an aspect, a method of retarding, preventing, and ameliorating disease or a medical affliction in a subject comprises analyzing a biological sample taken of a subject for TG molecular analysis by ESI/MS/MS with neutral loss scanning and prescribing a therapy for the subject based on that TG molecular species determination. In an aspect, the subject is human.

BRIEF DESCRIPTION OF THE DRAWINGS

More in detail, FIGS. 1A and 1B depict positive-ion electrospray ionization mass spectrum of an equimolar mixture of triaglycerides. FIG. 1A depicts an ESI/MS analysis of an equimolar mixture of twelve species of TG. FIG. 1B depicts an ESI/MS of six triglyceride species.

FIGS. 2A and 2B depict a relationship of ESI/MS relative peak intensities with TG molecular species concentration.

FIGS. 3A and 3B depict positive-ion electro spray ionization tandem mass spectra of triglyceride molecular species in the product ion mode. FIG. 3(A) depicts an ESI tandem mass spectrum of lithiated 16:0/18:1/20:4 TG. FIG. 3B depicts an ESI tandem mass spectrum of lithiated 18:1/20:4/18:1 TG.

FIG. 4 depicts a positive-ion electrospray ionization mass spectrum and tandem mass spectra of an equimolar mixture of triglycerides by neutral loss scanning.

FIG. 5 depicts a positive-ion electrospray ionization mass spectrum and neutral loss mass spectra of lipid extracts from rat myocardium.

DETAILED DESCRIPTION OF THE INVENTION

Figure 1:
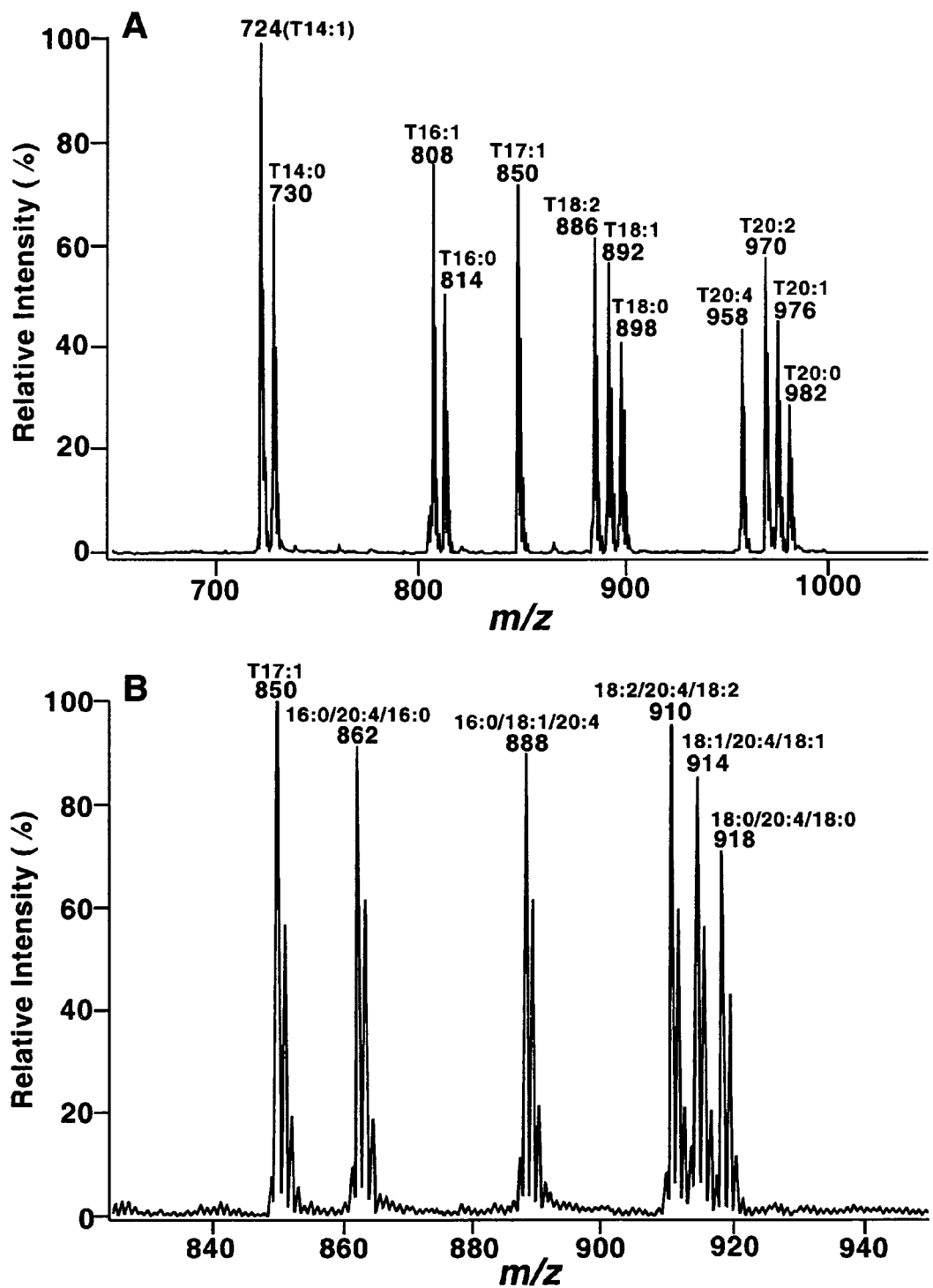
FIGS. 1A and 1B, FIGS. 2A and 2B, FIGS. 3A and 3B and FIGS. 4-5 depict analytical results of tests conducted using the inventive ESI/MS/MS process herein.

The present invention is understood more readily by reference to the following detailed description of the invention and the Example included therein.

Before the present method and kit are disclosed and described, it is to be understood that this invention is not limited to specific apparatus or to a specific method. It is also to be understood that the terminology used herein is for the purpose of describing particular embodiments only and is not intended to be limiting.

It must be noted that, as used in the specification the singular forms "a," "an," and "the" include plural referents unless the context clearly dictates otherwise.

In an aspect, the term "patient" includes subject and individual. In an aspect, the patient includes a human, feline, canine, horses and murine.

In an aspect, the invention comprises a rapid, simple, and reliable method for the quantitative analysis and molecular species fingerprinting of triglycerides (TG) directly from chloroform extracts of biological samples.

In an aspect, a method for the determination of triglyceride (TG) content and/or molecular species composition of matter in a mammalian and plant biological sample comprises subjecting said biological sample to lipid extraction to obtain a lipid extract and subjecting the lipid extract to electrospray ionization tandem mass spectrometry (ESI/MS/MS) providing the TG mass and individual molecular species content as an output.

In an aspect, a biological sample comprises a sample taken of at least one of blood, vessels, atheroma, liver, stool and other body tissues as well as biopsies of body organs such as a liver biopsy or a muscle biopsy.

As used here, the term "contour analysis" is an analysis based on the shape or periphery of the outline of data, such as external periphery on a 2 dimensional drawing. In an aspect, a contour is presented in some Figures of this application.

In an aspect the inventive method provides for mass accuracy of detecting and quantifying specific components of a biological sample via a systematic toxicological analysis using a mass spectrometer/mass spectrometer herein after referred to as a tandem mass spectrometer.

In an aspect, the term "deconvulution" includes the use of appropriate deconvuluting algorithms which provide for a systematic procedure for removing noise, extraneous signals and haze from output of a device such as from the output of an ESI/MS/MS. In an aspect, an illustrative useful deconvolution method is present in the Examples. Use of the deconvolution algorithms provides a deconvoluted determination.

In an aspect the inventive methodology comprises a total analysis of triglyceride individual composition of matter of each triglyceride molecular species of each triglyceride molecular species in a biologic sample through a high throughput procedure.

Briefly, the inventive methods present a novel two-dimensional approach/method which quantitates individual molecular species of triglycerides by two dimensional electrospray ionization mass spectroscopy with neutral loss scanning. This method provides a facile way to fingerprint each patient's (or biologic sample's) triglyceride composition of matter (individual molecular species content) directly from chloroform extracts of biologic samples. Through selective ionization and subsequent deconvolution of 2D intercept density contours of the pseudomolecular parent ions and their neutral loss products, the individual molecular species of triglycerides can be determined directly from chloroform extracts of biological material. This 2D (two dimensional) approach comprises a novel enhanced successful functional therapy model for the automated determination and global fingerprinting of each patient's serum or cellular triglyceride content thus providing the facile determination of detailed aspects of lipid metabolism underlying disease states and their response to diet, exercise or drug therapy.

Lipids are essential cellular constituents that have multiple distinct yet critical roles in cellular function. Lipids provide an impermeable barrier which separate intracellular and extracellular compartments without which life and self-renewal would be impossible. Moreover, lipids concurrently provide a matrix for the appropriate interactions of membrane-associated proteins to interact with each other as well as promote interactions of membrane proteins with cognate intra- and extracellular binding partners. Finally biologic membranes serve as storage reservoirs for biologically active 2nd messengers (eicosanoids, diglycerides, ceramides, etc) that allow each cell to effectively respond to internal and external stimuli. Biologic membranes fulfill these multiple functions through the synthesis of multiple distinct covalent entities each with its unique structural and physical characteristics. The inherent chemical diversity present in biologic lipids is achieved through multiple discrete covalent assemblies of lipid backbone (typically glycerol) with linear combinations of various aliphatic chains (typically 14-22 carbons long containing variable amounts of unsaturation). This biologic diversity facilitates the specific tailoring of individual cellular responses to alterations in cellular nutrient status, metabolic history and signaling events. Accordingly, many groups have rigorously pursued the identification of alterations in cellular lipid constituents to identify the chemical mechanisms underlying such diverse diseases as obesity, atherosclerosis and lipotoxicity now endemic in industrialized populations.

The precise complement of chemically distinct covalent entities in cellular lipids has been referred to as the cellular lipidome. Research in lipidomics incorporates multiple different techniques to first quantify the precise chemical constituents present in the cellular lipidome, determine their subcellular organization (subcellular membrane compartments and microdomains) and delineate lipid-lipid and lipid-protein conformational space and dynamics. Through these methods, the role of lipids in biologic processes can ultimately be determined. The first step in global lipidomics is to obtain a detailed account of the precise chemical entities (i.e. composition of matter) present in a cell's lipidome and identify alterations that precipitate, or are associated with, phenotypic alterations after cellular perturbation.

In an aspect of this inventive method, we employ tandem mass spectroscopic separation of specific lipid class-reagent ion pairs is used in conjunction with contour density deconvolution of cross peaks resulting from neutral losses of aliphatic chains to determine the individual triglyceride molecular species from a biological sample (blood, liver, muscle, feces, urine, tissue biopsy, or rat myocardium.).

As used herein the term "tandem mass spectrometer" includes a functional analytical instrument having the technical capability to capably measure the mass of molecules, identify those molecules and provide such identifying information in digitized or hard copy output format.

As used herein the term "fingerprinting" includes a biological sample analysis including quantification and qualification of the numbers and types of TG molecular species present in a biological (biologic) analyzed sample. In an aspect, the sample is a biological sample form a mammal or a plant.

In an aspect, a TG molecular species determination comprises a determination of at least one TG in a biological sample. In an aspect, the TG molecular species determination comprises the determination of 2, 3, 4, 5, 6, 7, 8, 9, 10 TG molecular species in a biological sample.

As used herein, the term "triglycerides", denoted symbolically as TG, includes the alpha and beta forms, multiple beta' and beta forms, single, multiple and mixed acyl triglycerides and triglyceride mixtures and includes compounds having three glycerol residues (e.g. cardiolipin). TG includes molecules of glycerol esterified with three fatty acids and corresponding ether or oxidized molecular species. As used herein, the term "acyl" refers to an organic acid group in which the —OH of the carboxyl group is replaced by some other substituent. Useful non-limiting TG include compounds in which three aliphatic chains are linked to a glycerol independently with ester, ether, and/or vinyl ether linkage.

As used herein the term "TG molecular species profile" includes the relative and actual distribution of TG molecular species composition of matter in a biological sample such as in a mammalian or plant living cell having a genome.

Abbreviations used herein include DAG, diacylglyceride; DMAP, N,N-dimethyl-4-aminopyridine; Dm:n DAD, di m:n glyceride; ESI, electrospray ionization; FA, fatty acid; MS/MS tandem mass spectrometry; m:n, fatty acyl chain containing m carbons and n double bonds; NL, neutral loss; TG, tracyglycerides; Tm:n TG and tri m:n glyceride.

As used herein, the term "m" represents an integer in the range from about 1 to about 22. As used herein the term "n" independently of m represents an integer from about 0 to about 6 such as independently integers 1, 2, 3, 4, 5 and 6.

As used herein, the term "biological sample" includes a sample of a suitable size such as a sample of size and composition suitable to a TG analysis of biological matter. In an aspect the biological sample includes serum, blood, urine, mammalian and human bodily fluid and a cell, such as a mammalian cell or a recombinant cell, a native or modified mammalian cell In an aspect, bodily fluid comprises a solid, semi-solid, liquid or semi-liquid mass exiting or excreted from the human body.

As used herein the term "mass spectrometer" includes and is synonymous with the term mass analyzer and may be used interchangeably herein.

In an aspect a biological sample comprises a composition comprising TG which is nonantagonistically accommodating to a TG analysis using ESI and tandem mass spectrometry.

As used herein the term "agent" includes atoms, cells and molecules.

As used herein, the term "normalization" include a method where peaks or numbers of an output are proportionally calculated or plotted to a selected peak or number which is generally arbitrarily assigned a value such as 1 or 100.

In an aspect one mass analyzer is connected to another sequentially coupled mass analyzer mechanically by an interpositioned chamber (the chamber referred to as a collision cell or chamber) that can break a molecule undergoing analysis and emitted by the first mass analyzer into two or more component parts. In an aspect a tandem mass spectrometer comprises first and second sequentially coupled mass analyzers. The biological sample is a sample representative of a portion of the subject such as of a human, wherein the result of having a TG analysis presents a meaningful point of medical research or treatment to one taking or having the biological sample taken and analyzed. In another aspect a tandem mass spectrometer comprises a first, second and third sequentially coupled mass analyzers.

Advantageously, tandem mass spectrometry (MS/MS) is accurate and specific in its identification of TG individual molecular species. Tandem mass spectrometry analyzes small amounts of biological sample and provides a multi-component analysis simultaneously or nearly simultaneously of a biological sample in an elapsed analysis time of about two to three minutes or so.

In an aspect the weight of a biological sample is at a minimum of tissue about 1 mg, of cells about 2,000, and of blood about 2 µl or comparable functionally adequate amounts, quantities or volumes of other biologic samples. In an aspect, the amount of biological sample is that amount or volume which is sufficient to provide for an analysis.

In an aspect, a biological sample is processed in tandem mass spectrometer a first mass spectrometer set up in a tandem arrangement with another mass spectrometer. In that regard the biological sample can be considered as sorted and weighed in the first mass spectrometer, then broken into parts in an inter-mass spectrometer collision cell, and a part or parts of the biological sample are thereafter sorted and weighed in the second mass spectrometer thereby providing a mass spectrometric output readily and directly useable from the tandem mass spectrometer.

In an aspect, the output of the tandem mass spectrometer which is TG molecular species determination, is presented visually and optionally and can be recorded on a recorder output. Typically the tandem mass spectrometer output is shown or displayed visually as an abscissa and ordinate graph having ordinate lines spread across an abscissa at a right angle to each other such as on a display or graphic surface visible to the eye. This organized display output is a mass spectrum. The point at which the vertical line occurs in the spectrum is the place which identifies a compound's mass while the height of that vertical line associated with the analyzed compound represents the amount of the compound present in the biological sample fed to the mass spectrometer. Typically, the biological sample is fed by hand or robotics to the ESI/tandem mass spectrometer.

In analysis, a sample is generally taken of the subject to be analyzed. In an aspect, the sample is part of, or the entire subject to be analyzed. In an aspect a subject to be sampled comprises a plant. In another aspect the subject comprises an animal such as a human, porcine, feline, equistrine and murine, a part or portion thereof.

If desired, samples can be prepared by chromatography or other purification methods as well, prior to analysis with electrospray ionization tandem mass spectrometry (ESI/MS/MS).

In an aspect, a pre-analysis separation comprises a separation of lipoproteins prior to lipid extraction. In an aspect, the pre-analysis separation comprises at least one operation or process which is useful to provide an enhanced biological sample to the electrospray ionization tandem mass spectrometry (ESI/MS/MS). In an aspect, a pre-analysis separation is performed on a biological sample and two compositions are prepared accordingly from the biological sample. In an aspect one composition comprises high density lipoproteins and another composition comprises low density lipoproteins.

Generally, a biological sample taken is representative of the subject from which or of which the sample is taken so that an analysis of the sample is representative of the subject. In an aspect a representative number of samples are taken and analyzed of a subject such that a recognized and accepted statistical analysis indicates that the analytic results are statistically valid. Typically the composition is aqueous based and contains proteinaceous matter along with triglycerides. For example, a human blood sample is sometimes used. Through use of this inventive method, a plasma sample can be analyzed and appropriate information from the plasma can be extracted in a few minutes. Alternatively, information can be taken from the cells in the blood as well.

In an aspect, serum is utilized as a biological sample. After whole blood is removed from a human body and the blood clots outside the body, blood cells and some of the proteins become solid leaving a residual liquid which is serum.

In an aspect a control sample is employed in the analysis.

In an aspect, the biological sample or a representative aliquot or portion thereof is subjected to lipid extraction to obtain a lipid extract suitable for ESI/MS/MS. In an aspect lipids are extracted from the sample which in an aspect contains a tissue matrix. Non-lipid contaminants should be removed from the lipid extract.

In one aspect lipid extraction is carried by the known lipid extraction process of Folch as well as by the known lipid extraction process of Bligh and Dyer. These useful lipid extraction process are described in Christie, W. W. Preparation of lipid extracts from tissues. In: Advances in Lipid Methodology—Two, pp. 195-213 (1993) (edited by W. W. Christie, Oily Press, Dundee) EXTRACTION OF LIPIDS FROM SAMPLES William W. Christie The Scottish Crop Research Institute, Invergowrie, Dundee DD2 5DA, Scotland all of which are incorporated herein in their entirety by reference. The useful Folch extraction process is reported at Folch et al., J Biol Chem 1957, 226, 497 which is incorporated herein in its entirety by reference.

Generally, lipid extraction is carried out very soon in time on the tissue matrix or immediately after removal (harvest) of tissues (tissue matrix) from humanely sacrificed organisms which have been living (carried out using and following acceptable animal welfare protocols). Alternatively, tissues are stored in such a way that they are conservatively preserved for future use. In an aspect, a lipid extract is provided and used to produce ionized atoms and molecules in the inventive analytical method as feed to the ESI n our novel analysis method.

In an aspect a chloroform lipid extract is employed as a lipid extract composition fed to the ESI. The effluent from theESI is fed to the tandem mass spectrometer (i.e. from the exit of the ESI).

In an aspect, a Freezer Mill 6800 from Fisher Bioblock Scientific is used to finely pulverize soft or hard harvested tissues of a biological sample in one or two minutes in liquid nitrogen to render the tissue sufficiently pliable and porous for lipid extraction. Alternatively, the pulverization of the harvested tissue is carried out by subjecting the harvested tissue to hand directed mashing and pulverization using a hand directed stainless-steel mortar and pestle. In a further aspect, an enzymatic digestion is carried out on the harvested tissue which is harvested from a preserved cadaver.

In an aspect, lipids are contained in the lipid extract following the lipid extraction. Generally the extraction is a suitable liquid/liquid or liquid/solid extraction whereby the TG are contained in the extract. In an aspect the extractant has sufficient solvating capability power and solvating capacity so as to solvate a substantial portion of the TG therein or substantially all of the TG present in the biological sample and is contained in the lipid extract.

In an aspect, chloroform is employed as an extractant to produce a useful lipid extract. Other useful extractants include but are not limited to those extractants which have a solvating power, capability and efficiency substantially that of chloroform with regard to the TG molecular species.

The inventive process creates charged forms of very high molecular weight TG molecules obtained via lipid extraction of a biological sample as a part of the process of detecting and analyzing biological samples containing TG.

In an aspect, in order to detect for and analyze ionized atoms and molecules such as TG molecular species in a biological sample, the lipid extract of that biological sample is used to produce ionized atoms and molecules by an ionization method such as electrospray ionization (ESI). As used herein, the term ESI includes both conventional and pneumatically-assisted electrospray.

In use, the inventive procedure operates by producing droplets of a sample composition by pneumatic nebulization which compresses and forces a biological sample composition containing TG such as an analyte containing TG into a proximal end of a mechanical means housing or holding a fine sized orifice such as a needle or capillary exiting at the distal end of the orifice at which there is applied a sufficient potential. Generally the orifice is a very small bore full length orifice having an internal average diameter or bore in the range from about 0.2 to about 0.5 mm.

In an aspect formation of a suitable spray is a critical operating parameter in ESI. Suitable solvent removable filters may be used to remove undesired solvents in the biological sample composition prior to being fed to the ESI. Generally high concentrations of electrolytes are avoided in samples fed to ESI.

The composition of materials of the means housing or holding the orifice and the orifice are compatible with the compositions of the biological sample to be processed through the orifice. Metallic and composition plastic compositions may be employed. In an aspect the orifice is a capillary or has a conical or capillary shape. In another aspect the orifice is cone shaped with the exterior converging from the proximate end to the distal end.

In an aspect the biologic sample is forced through the orifice by application of air pressure to the sample at the proximate end of the orifice or the sample is forced through the orifice or capillary by the application of vacuum at the distal end of the orifice. The net result is that ions are suitably formed at atmospheric pressure and progress through the cone shaped orifice. In an aspect the orifice is a first vacuum stage and the ions undergo free jet expansion. A collector at the distal end of the orifice collects the ions and guides the ions to a tandem mass spectrometer (MS/MS).

As used herein, the terms biologic samples and biological sample are synonymous with regard to one another and are used interchangeably.

In an aspect a suitable potential is applied via a field to the sample composition discharged from or at the distal end of the orifice. This potential is sufficiently high so that it capably and effectively converts the composition exiting the distal end of the orifice into a fine spay of droplets all at the same or substantially the same potential. See http://methods.ch.com.ac.uk/meth/ms/theory/esi.html for a description of ESI which is incorporated herein by reference in its entirety. The potential is in the range from about 3 to about 5 kv (kv is kilovolts).

ESI is followed by tandem mass spectrometry (MS/MS) which is an analytical method to separate and measure charge to mass ratios (M/Z) of ionized molecules and/or atoms. See http://nanogenesys.maxbizcenter.comm/new2183.html. In an aspect a tandem mass spectrometer is utilized which quantifies the amounts of individual ionized atoms or molecules and as noted in the above web site provides detailed information on structure of molecules of the sample undergoing analysis therein.

In another aspect, ESI useful herein is also described at http://chm.bris.ac.uk/omsf/interface.html wherein a sample solution is described as being sprayed across a highly protected diffuser of a few kilovolts from a needle into an orifice in an interface. Thereafter according to that web site (The NERC Organic Mass Spectrometry Facility) heat and gas fumes are used to desolvate ions in the sample solution undergoing ESI.

In an aspect, a tandem mass spectrometer is employed and is fed the biologic sample affluent from the ESI. The tandem mass spectrometer is an instrument that detects molecules by measuring their weight (mass). Mass spectrometers measure weight electronically and display output analytical results in the form of a mass spectrum. In an aspect, mass spectrum is the readable and visual output of a mass spectrometer a.e., a graph, in digital or hard copy form that shows each specific molecule by weight and how much of each molecule is present in the sample which was fed to the tandem mass spectrometer for analysis therein.

In an aspect collision activated dissociation is employed in preparing the feed composition (i.e. sample from the ESI) to the tandem mass spectrometer. A useful reference on tandem mass spectrometry is Mass Spectrometry/Mass Spectrometry: Techniques and Applications of Tandem Mass Spectrometry, Busch, K. L., Glish, G. L., McLuckey, S. A., ISBN: -471-18699-6, Hardcover, January 1989. This reference is incorporated herein by reference in its entirety.

In an aspect, the ESI/MS/MS is powered by 110 volt electrical supply. To turn on, a user connects the ESI/MS/MS to an electric power supply and turns on the appropriate electrical switches providing current to the ESI/MS/MS.

In an aspect, tandem mass spectrometry provides the needed specificity and selectivity for analysis of TG molecular species including trace analysis in complex biological samples including complex tissue analysis of such biological samples comprising TG.

Advantageously, the inventive methods herein comprise an unexpected but successful translation of an enhanced analytical procedure comprising ESI/MS/MS for TG molecular species determination of a biological sample providing high throughput global fingerprinting of each patient's serum or cellular triglyceride molecular species facilitate or optimize medicinal therapies for subjects.

In an aspect, deconvolution is carried out by applying any useful and acceptable deconvolution algorithm to the output of the ESI/MS/MS providing as a result a deconvoluted data output product.

In an aspect, data is normalized by applying a mathematically and statistically useful and acceptable normalization technique to deconvoluted data output product providing as a result normalized data output.

In an aspect, appropriate computer software and hardware is provided and is programmed to provide appropriate deconvolution and normalization as aforedescribed using appropriate devonvolution and optionally normalization algorithms.

The following Examples are presented merely to further illustrate and explain the present invention and should not be taken as limiting the invention in any regard.

EXAMPLES

The present invention is more particularly described in the following Examples which are intended as illustrative only since numerous modifications and variations therein will be apparent to those skilled in the art. All weights and ratios used herein are on a weight basis unless otherwise specified.

Materials and Methods

A. Materials Obtained and Sources

In this Example, triglycerides (TG) were employed as illustrative.

All triglycerides containing three homogeneous acyl chains including tritetradecanoin (T14:0 TG), tritetradecenoin (T14:1 TG), trihexadecanoin (T16:0 TG), trihexadecenoin (T16:1 TG), triheptadecenoin (T17:1 TG), trioctadecanoin (Ti8:0 TG), trioctadecenoin ($\Delta 9$ cis) (T18:1 TG), trioctadecadienoin ($\Delta 9$, 12 cis) (Ti8:2 TG), trieicosanoin (T20:0 TG), trieicosenoin ($\Delta 11$ cis) (T20:1 TG), trieicosadienenoin ($\Delta 11$, 14 cis) (T20:2 TG), and trieicosatetraenoin ($\Delta 5$, 8, 11, 14 cis) (T20:4 TG) and all 1,3-diacylglycerides (DAG) containing two homogeneous acyl chains including dihexadecanoin (D16:0 DAG), dioctadecanoin (D18:0 DAG), diotadecenoin ($\Delta 9$ cis) (D18:1 DAG), and dioctadecadienoin ($\Delta 9$, 12 cis) (D18:2 DAG) were purchased from Nu Chek Prep, Inc. P.O. Box 295, Elysian, Minn. 56028. All TG molecular species containing mixed acyl chains including 1-octadec-9'-enoyl-2,3-dihexadecanoyl-rac-glycerol (18:2/16:0/16:0 TG), 1-octadecanoyl-2,3-dihexadecanoyl-rac-glycerol (18:0/16:0/16:0 TG), 1-hexadecanoyl-2-octadecanoyl-3-hexadecanoyl-rac-glycerol (16:0/18:0/16:0 TG), 1-hexadecanoyl-2-octadex-9'-enoyl-3-octadecanoyl-rac-glycerol (16:0/18:1/18:0 TG), 1-hexadecanoyl-2-octadecanoyl-3-octadec-9'-enoyl-3-octadecanoyl-rac-glycerol (16:0/18:1/18:0 TG), 1-hexadecanoyl-2-octadecanoyl-3-octadec-9'-enoyl-rac-glycerol (16.0/18:0/18:1 TG), and 1,2- octadec-9'-enoyl-3-octadecanoyl-rac-glycerol (18:1/18:1/ 18:0 TG) were obtained from Matreya, Inc. (2011 Pine Hall Drive, State College, Pa. 16803, also in Pleasant Gap, Pa.). 1-Hexadecanoyl-2-octadec-9'-enoyl-sn-glycerol (16:0/18:1 DAG) were purchased from Avanti Polar Lipids, Inc. (700 Industrial Park Drive, Alabaster, Ala.).

The purity of all TG (commercial and synthetic) was determined by ESI/MS prior to use in quantitative analyses. All solvents were HPLC grade (or higher) and were obtained from Fisher Scientific (Pittsburgh, Pa.). Reagents were of analytical grade and were purchased from Sigma-Aldrich 2909 Laclede St. Louis, Mo. 63103.

B. Synthesis and Purification of TG Molecular Species Containing Arachidonoyl Constituents The reaction procedure was performed in a dry nitrogen atmosphere at 22° C. and care was taken to minimize exposure of the reaction vessel to light. Ten milligrams of each individual DAG molecular specie[D16:0 DAG, D18:0 DAG, D18:1 DAG, D18:2 DAG, and 16:0/18:1 DAG, stored in chloroform/methanol (2/1, v/v)] was dried under a nitrogen stream. Dried DAGs and recrystallized N,N-dimethyl-4-aminopyridine (DMAP) were further individually dried under high vacuum overnight in the presence of phosphorus pentoxide. Each individual DAG molecular species was dissolved in 1 mL of freshly distilled chloroform in a 5-mL conical vial prior to the addition of 3 mg of re-crystallized DMAP in solid. Next, 15 mg of arachidonoyl chloride (previously dissolved in 1 mL of distilled chloroform) was added dropwise to the reaction vessel over 10 min with constant stirring. The reaction mixture was stirred for an additional 30 min prior to termination by addition of distilled water and subsequent Bligh and Dyer extraction.

Synthetic arachidonoyl-containing TG molecular species were purified by TLC (silica LK6D plates, Whatman) employing a mobile phase comprised of petroleum ether/ethyl ether/acetic acid (80/20/1 v/v/v). The band on the TLC plate corresponding to TG molecular species, which was recognized by comparison to a TG standard spotted on the side of the same plate, was scraped, the silica powder was loaded onto a pre-rinsed Sep-Pak silica column, and TG molecular species were eluted utilizing 10 mL of chloroform. Purified arachidonoyl-containing TG molecular species were quantitated by capillary gas chromatography after acid methanolysis utilizing arachidonic acid (20:0) as an internal standard (23).

C. Preparation of the Mixtures of TG Molecular Species

A stock solution of each TG molecular species in chloroform was quantitatively prepared and stored under nitrogen at −20° C. The TG solutions were brought to room temperature (or 25° C.) just prior to utilization. Mixtures of TG molecular species were prepared from these stock solutions using gas-tight syringes. The concentration of each TG molecular species in the mixtures was ranged from 1 to 1000 nM. Since sodium ions could complicate the ESI mass spectra of TG and interfere with the quantitative analyses of TG molecular species, all the mixed solutions were extracted by a modified Bligh and Dyer technique (24) utilizing 50 mM LiOH in an aqueous layer to minimize the presence of sodium ion in the solutions. The extracts were dried under a nitrogen stream, dissolved in chloroform, filtered with 0.2 μm Gelman acrodisc CR PTFE syringe filters (Gelman Science, Ann Arbor, Mich.), and dried under a nitrogen stream. The final residues of TG mixtures were resuspended in 0.2 mL of 1:1 chloroform/methanol for ESI/MS analyses.

D. Preparation of Lipid Extracts From Rat Heart Tissue

Male Sprague-Dawley rats (a universally used, widely accepted and general purpose research model rat of about 350-450 grams body weight) were purchased from Charles River Laboratories, Inc (251 Ballardvale Street Wilmington, Mass. 01887-1000) and humanely sacrificed according to accepted animal welfare protocols.

The Sprague-Dawley rat hearts were excised quickly and immersed in ice-cold buffer (250 mM sucrose/25 mM imidazole, pH 8.0, at 4° C.). After removing extraneous tissue and epicardial fat, each heart tissue was blotted to remove excess buffer and immediately freeze-clamped at the temperature of liquid nitrogen. Myocardial wafers were pulverized into a fine powder with a stainless-steel mortar and pestle. A protein assay was performed on homogenized myocardial wafers and data were normalized to the protein content of the rat heart tissues. A ~30 mg myocardial wafer was weighed from each harvested rat heart and lipids were extracted by a modified Bligh and Dyer technique (24) utilizing 50 mM LiOH in an aqueous layer in the presence of T17:1 TG (150 pmol/mg of protein; used as an internal standard for TG quantification). This molecular species of endogenous TG represents <1% of lipid mass. ESI mass spectra from control experiments in which the internal standard was not exogenously added were also taken to ensure the absence of any demonstrable endogenous molecular ions in that region. The lipid extracts were dried under a nitrogen stream, dissolved in chloroform, desalted with Sep-Pak columns, filtered with 0.2, μm Gelman acrodisc CR PTFE syringe filters (Gelman Science), reextracted, and dried under a nitrogen stream. The final lipid residue was resuspended in 0.2 μL of 1:1 chloroform/methanl for ESI/MS analyses.

E. Electrospray Ionization Mass Spectrometry of Triglycerides (TG)

ESI mass spectral analyses of TG molecular species were performed similarly to the analyses of phospholipids utilizing a Finnigan TSQ-7000 spectrometer equipped with an electrospray ion source as described previously (25, 26). (Thermo Finnigan, Global Headquarters, 355 Fiver Oaks Parkway, San Jose, Calif. 95134-1991 USA).

Typically, a 5-min period of signal averaging in the profile mode was employed for each (mass spectrum)s of a TG sample or lipid extract. All samples were appropriately diluted in 1:1 chloroform/methanol prior to direct infusion into the ESI chamber using a syringe pump at a flow rate of 1 μL/min. TG molecular species were directly ionized in the positive-ion mode by ESI. Tandem mass spectrometry of TG after electrospray ionization of TG after electrospray ionization was performed by collisional activation with argon gas. The resultant product ions were analyzed after passage into the third quadrupole. The degree of collisional activation as adjusted through variation of the cd offset voltage and collision gas pressure. During this study, a collision energy of 35 eV and collision gas pressure of 2.5 mTorr were used. Two types of tandem mass spectrometric analyses were employed (i.e., product-ion scanning and neutral loss scanning). Product-ion tandem mass spectrometry was conducted similarly as described previously (27). Tandem mass spectrometry utilizing neutral losses were performed through the simultaneous scanning of both the first and third quadrupoles at a fixed different mass (i.e., neutral loss) corresponding to the mass of the fatty acids of interest.

TG molecular species were directly quantitated by comparisons of ion peak intensities with that of internal standard (i.e., T17:1 TG) after correction for C isotope effects in the positive-ion mode. Two types of $^{13}C$ isotope effects were considered. First, correction for the effect from the carbon number difference between a given TG molecular species and the internal standard was calculated as follows:

$$Z_1=(1+0.011n+0.011^2n(n-1)/2)/(1+0.011s+0.011^2 s(s-1)/2)=0.5648+6.213\times10^{-3}n+3.417\times10^{-5}n^2, \quad [1]$$

where $Z_1$ is a type I $^{13}C$ isotope correction factor, n is the total carbon number in the molecular species of interest, and s is the total carbon number of internal standard, and s is 54 for T17:1 TG. n is in the range from about 0 to about 6.

The degree of type I isotope correction is less than 10% in most cases. The second type of $^{13}C$ isotope effect comes from the overlapping of the M+2 isotope peak with the molecular ion peak of a species, which has a 2-Da higher mass. The general correction factor for this type of $^{13}C$ isotope effect is as follows:

$$Z_2 = 1-(I_{m-2}/I_m)0.011^2m(m-1)/2 = \\ 1-6.05\times10^{-5}m^2(I_{M-2}/I_M), \quad [2]$$

where $Z_2$ is a type II $^{13}C$ isotope correction factor, m is the total carbon number in the molecular species with lower molecular mass, and m ranges from about 30 to about 70 and $I_{M-1}$ and $I_M$ are peak intensities of ions at molecular weight (M−2) and M, respectively.

As used herein, the alphabetical symbols m, n, s represent integers which vary independently of each other and may be the same or different. As used herein, "C" means carbon 13 isotope.

Protein concentration was determined with a bicinchoninic acid protein assay kit (Pierce Biotechnology, Inc., P.O. Box 117, Rockford, Ill., 61105) using bovine serum albumin as a standard. Quantitative data from biological samples were normalized to the protein content of the tissues and all data are presented as means±SEM of a minimum of three independent preparations.

F. Results—Detailed Description of the Drawings

G. (FIGS. 1A and 1B, FIGS. 2A and 2B, FIGS. 3A and 3B, FIGS. 4-5 Depict Analytical Results of Tests Run Using the Inventive ESI/MS/MS Process Herein.)

FIG. 1 depicts positive-ion electrospary ionization mass spectrum of an equimolar mixture of triglycerides. Equimolar mixtures of 12 triglyceride molecular species (i.e., T14:1, T14:0, T16:1, T16:0, T17:1, T18:2, T18:1, T20:4, T20:2, T20:1, and T20:0, 10 nM each in a total volume of 200 μL) (A) or 6 triglyceride molecular species (i.e., 16:0/20:4/16:0, 16:0/18:1/20:4, 18:2/20:4/18:2 18:1/20:4/18:1, 18:0/20:4/ 18:0, and T17:1 TG, 10 nM each in a total volume of 200 μL) (B) were prepared from stock solutions and extracted by a modified Bligh-Dyer method in the presence of 50 nM LiOH in the acqueous phase as described herein under Materials and Methods.

The solutions of TG mixtures in chloroform/methanol (1:1, by volume) were directly infused into the ESI ion source using a Harvard syringe pump at a flow rate of 1 μL/min. Mass spectrometry of triglycerides was performed as previously described under Materials and Methods. Molecular ions in the mass spectra have been labeled with masses corresponding to their lithiated TG molecular species adducts. The masses of all ion peaks are rounded to the nearest integer.

Figure 2:
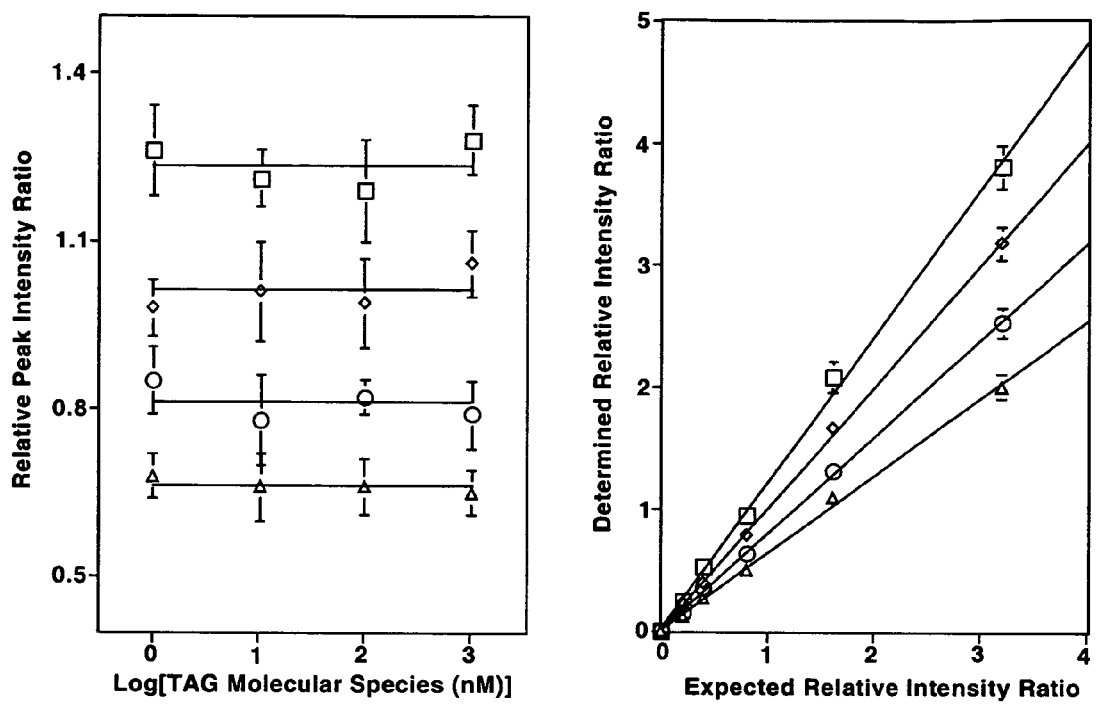

FIG. 2 depicts relationship of ESI/MS/relative peak intensities with TG molecular species concentration. In A, mixtures of TG molecular species containing identical molar ratios, but different concentrations, of individual TG components were prepared as described under Materials and Methods. Positive-ion ESI mass spectra were acquired as described in the legend to FIG. 1. The lithiated molecular ion peaks of each individual TG molecular species were quantified relative to the internal standard (T17:1 TG) after corrections were made for $^{13}C$ isotope effects. Experiments were performed over a three-order magnitude of concentration range (1 to 1000 nM) in mixtures containing T14:1 TG ( ), T16:1 TG (◇), T18:1 TG (○), or T20:1 TG (Δ). In B, samples were prepared containing different molar ratio relative to the internal standard (TI7:1) and the intensity of the molecular ion was quantified by ESI/MS after corrections for $^{13}C$ isotope effects. The ratios of molecular ion intensities of T14:1 TG ( ), T16:1 TG (◇), T18:1 TG (○), or T20:1 TG (Δ) with the molar ratio in the prepared solutions had coefficients ($\delta^2$)>0.99. The slope for each individual TG molecular species was defined as the correction factor for the sensitivity effect relative to T17:1 TG. Data are presented as a means±SEM from at least four separate sample presentations.

Figure 3:
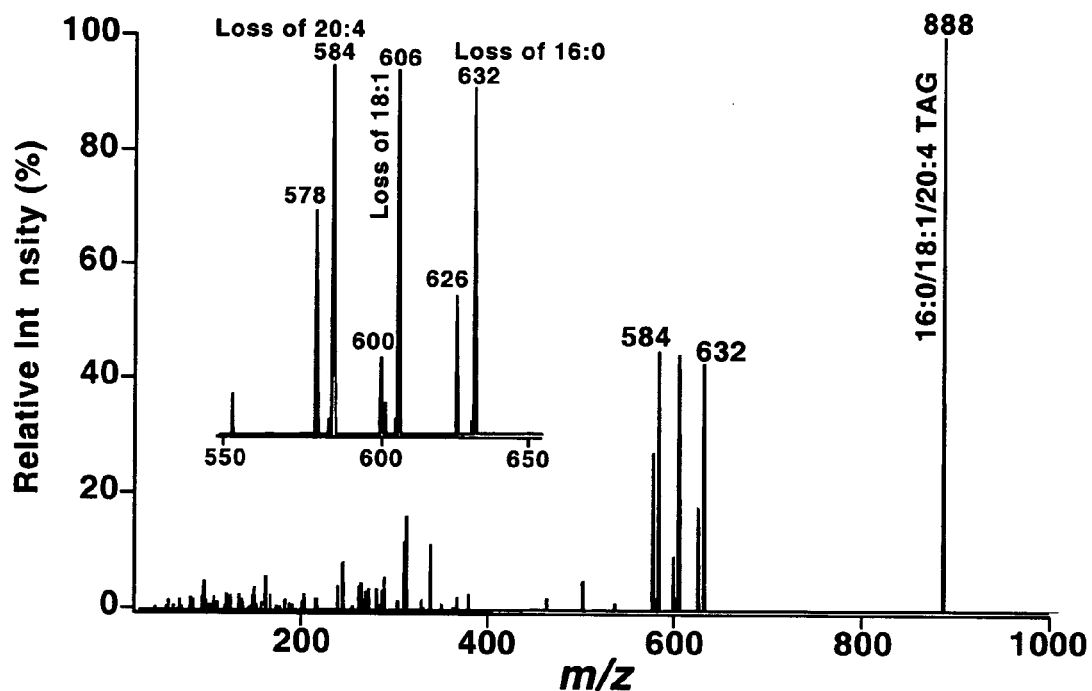
Figure 3:
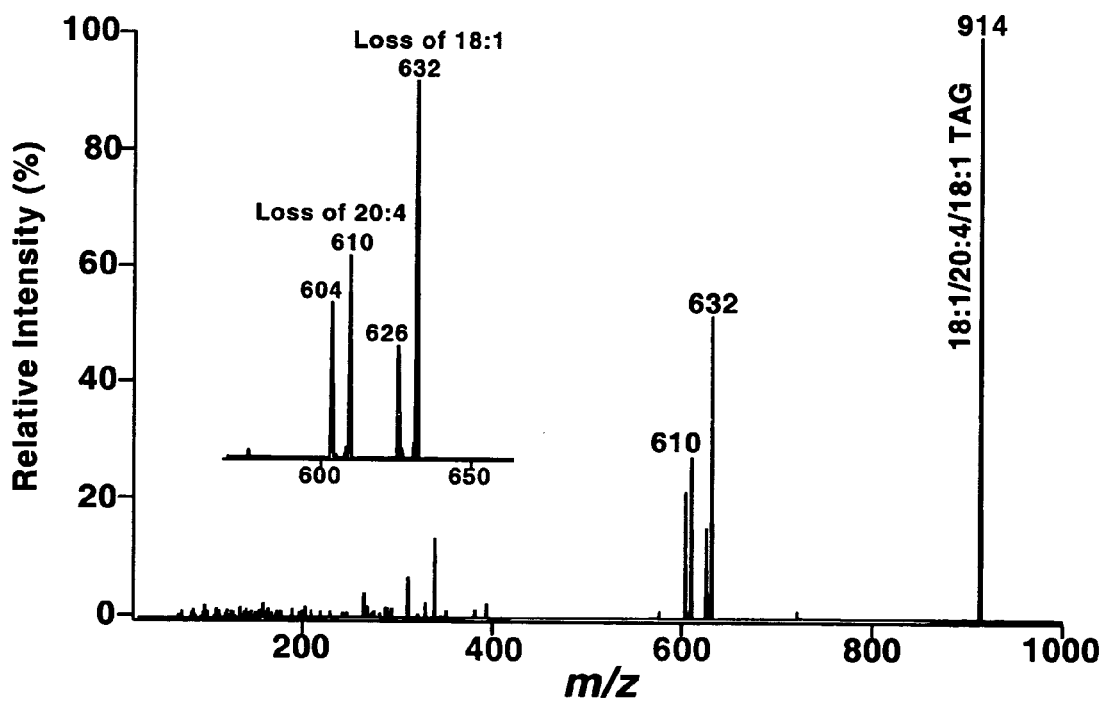

FIG. 3 depicts positive-ion electrospray ionization tandem mass spectra of triglyceride molecular species in the production mode. (A) ESI tandem mass spectrum of lithiated 16:0/18:1/20:4 TG. (B) ESI tandem mass spectrum of lithiated 18:1/20:4/18:1 TG. Samples of the TG mixture were prepared and ESI/MS was performed as described in the legend to FIG. 1. After selection of the lithiated pseudomolecular ion of TG molecular species in the first quadrupole, collision activation was performed in the second quadrupole and the resultant product ions were analyzed in the third quadrupole as described under Materials and Methods.

Figure 4:
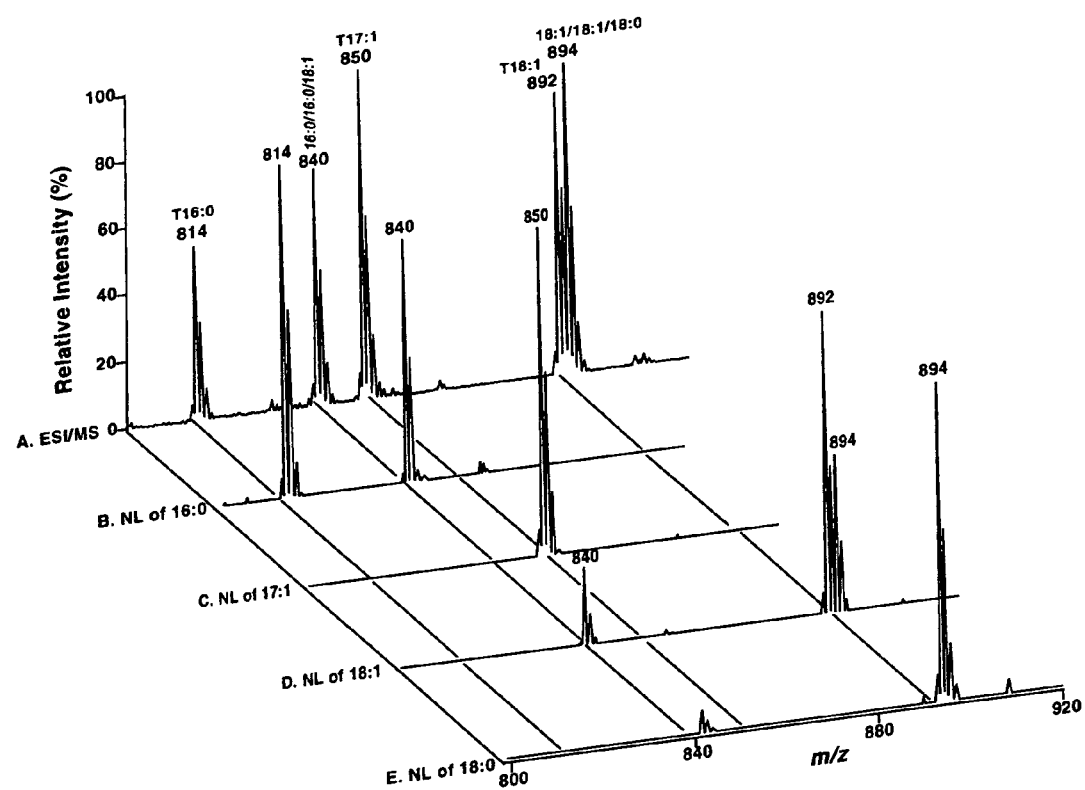

FIG. 4 depicts Positive-ion electrospray ionization mass spectrum and tandem mass spectra of an equimolar mixture of triglycerides by neutral loss scanning. An equimolar mixture of T16:0, 18:1/16:0/16:0, T17:1, T18:1, and 18:1/ 18:1;18:0 TG (2 pmol each in a total volume of 200 μL) was prepared from stock solutions and extracted by a modified method of Bligh-Dyer in the presence of 50 mM LiOH in the aqueous phase as described under Materials and Methods. The solution of the TG mixture (in chloroform/methanol, 1:1 volume) was directly infused into the ESI ion source using a Harvard syringe pump at a flow rate of 1 μL/min. Positive-ion ESI mass spectrum (Row A) of the mixture was acquired as described under Materials and Methods. Positive-ion ESI tandem mass spectra with neutral loss of 16:0 (Row B), 17:1 (Row C), 18:1 (Row D), and 18:0 (Row E) were acquired through simultaneous scanning of both the first and third quadrupoles at fixed different masses (neutral loss) as described under Materials and Methods. All NL mass spectra were displayed after normalization to the base peak in the individual spectrum. The total ion counts of each individual ion in all neutral loss mass spectra were determined from four individually prepared solutions and the averaged results are tabulated in Table 2.

Figure 5:
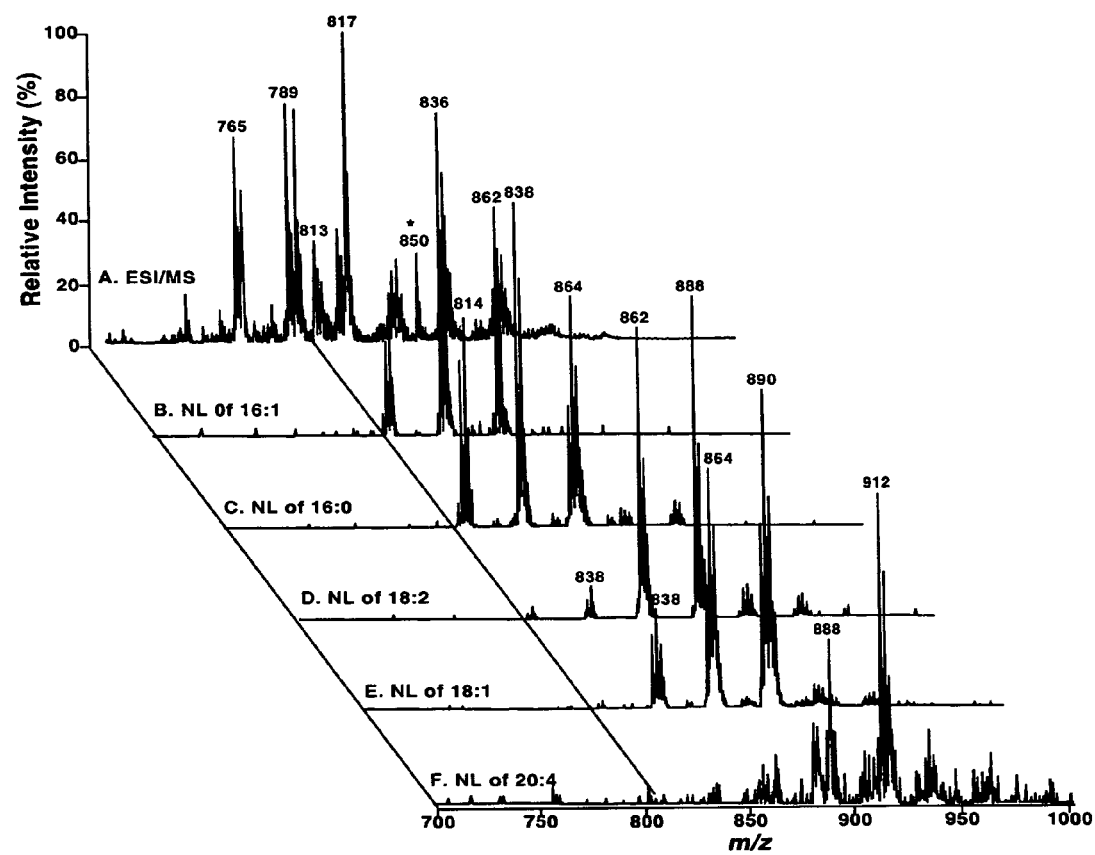

FIG. 5 depicts positive-ion electrospray ionization mass spectrum and neutral loss mass spectra of lipid extracts from rat myocardium. Lipid samples from rat myocrdium (~20 mg of wet tissue) were extracted by a modified method of Bligh-Dyer in the presence of 50 mM LiOH in the aqueous phase as described under Materials and Methods. Aliquots of the extracts in 1:1 chloroform/methanol were infused directly into the ESI source using a Harvard syringe pump at a flow rate of 1 μL/min. Positive-ion ESI mass spectrum (Row A) of lipid extracts was acquired as described under Materials and Methods. Positive-ion ESI tandem mass spectra of TG in lipid extracts with neutral loss of palmitoleic acid (16:1) (Row B), palmitic acid (16:0) (Row C), oleic acid (18:1) (Row D), linoleic acid (18:2) (Row E), and arachidonic acid (20:4) (Row F) were acquired through simultaneous scanning both first and third quadrupoles at fixed different mass values (neutral loss) as described under Materials and Methods. All NL mass spectra were displayed after normalization to the base peak in the individual spectrum. The total ion counts of each individual ion in mass spectra with neutral loss of each fatty acid were determined from four individually prepared mixture solutions and the averaged results are tabulated in Table 3. The internal standard peak (i.e. lithiated T17:1, TG) for TG quantification is indicated by the asterisk in Row A.

The data shown in the Figures is data of a tandem mass spectrum utilizing a neutral loss scanning. Data points on the ordinate(s) represent the number of ions (intensity) detected for a specific mass to charge ratio (mass to charge ratio is represented on the abscissa). The ion intensity at each mass to charge ratio is expressed relative to highest ion intensity at a specific mass to charge ratio. These ratios are expressed as a percent.

Multiple individual peaks are shown on the figures. Individual peaks are shown as one peak among many in the mass spectrum output. An individual peak represents a numerical count of the total ions detected at say m/Z 849.7. In an aspect, we read from the tandem mass spectrometer output that this peak is the largest peak in the mass spectrum (100% relative ion intensity). We assume in our applications that the charge is one, so that the mass of this lithiated molecule is 849.7 DA.

G. Quantitation of TG Molecular Species Using ESI/MS/MS

Our work has demonstrated that positive-ion ESI mass spectra of TG in the presence of lithium ion displayed predominant (>98%) lithiated TG molecular ions (8). However, the sensitivity of each TG molecular species in positive-ion ESI/MS was modestly (approximately 2-fold in the worst cases) dependent on the chain length and unsaturation index. For example, the positive-ion ESI mass spectrum of an equimolar mixture of T14:1, T14:0, T16:1, T16:0, T17:1, T1 8:2, T18:1, T18:0, T20:4, T20:2, T20:1, and T20:0 TG (10 nM for each molecular species) in the presence of LiOH displayed 12 molecular ion peaks with peak intensities which differed by at most 2-fold from internal standard, T17:1 TG (FIG. 1A). The sensitivity of each molecular species correlated with its unsaturation index and inversely correlated with its chain length. The intensity of each molecular species during positive-ion ESI mass spectra of TG was linear over a 1000-fold dynamic range examined (FIG. 2A).

Detailed analyses of the concentration-response profile of TG molecular species after correction for $^{13}C$ isotope effects demonstrated a strictly linear response which possessed different slopes for each molecular species relative to the internal standard (FIG. 2B). Accordingly, comparisons between different TG molecular species can be directly observed, but absolute quantitation requires consideration of factors which lead to the differential sensitivities between molecular species. The slope of the least-square regressive linear fitting for each individual TG molecular species was defined as the correction factor for the sensitivity effect relative to T17:1 TG and tabulated for each molecular species examined (Table 1 immediately below).

TABLE 1

Sensitivity Correction Factors of Common TG Molecular Species to T17:1TG

| TG Molecular Species | Determined Correction Factor | Calculated Correction Factor* |
|---|---|---|
| T14:0 (42:0) | 0.92 ± 0.10 | 0.91 |
| T14:1 (42:3) | 1.22 ± 0.05 | 1.34 |
| T16:0 (48:0) | 0.69 ± 0.06 | 0.69 |
| T16:1 (48:3) | 1.00 ± 0.08 | 1.02 |
| 16:0/16:0/18:1 (50:1) | 0.71 ± 0.05 | 0.73 |
| 16:0/18:0/16:0 (50:0) | 0.62 ± 0.09 | 0.63 |
| 18:0/16:0/16:0 (50:0) | 0.62 ± 0.07 | 0.63 |
| T17:1 (51:3) | 1 | 0.91 |
| 16:0/18:0/18:1 (52:1) | 0.65 ± 0.05 | 0.67 |
| 16:0/18:1/18:0 (52:1) | 0.65 ± 0.08 | 0.67 |
| 16:0/20:4/16:0 (52:4) | 0.90 ± 0.09 | 0.94 |
| T18:0 (54:0) | 0.54 ± 0.09 | 0.53 |
| 18:0/18:1/18:1 (54:2) | 0.66 ± 0.07 | 0.7 |
| T18:1 (54:3) | 0.81 ± 0.06 | 0.78 |
| 16:0/20:4/18:1 (54:5) | 0.89 ± 0.08 | 0.94 |
| T18:2 (54:6) | 0.93 ± 0.03 | 1.03 |
| 18:0/20:4/18:0 (56:4) | 0.72 ± 0.09 | 0.79 |
| 18:1/20:4/18:1 (56:6) | 0.85 ± 0.09 | 0.93 |
| 18:2/20:4/18:2 (56:8) | 0.96 ± 0.08 | 1.08** |
| T20:0 (60:0) | 0.44 ± 0.06 | 0.45 |
| T20:1 (60:3) | 0.66 ± 0.06 | 0.61 |
| T20:2 (60:6) | 0.87 ± 0.08 | 0.77 |
| T20:4 (60:12) | 0.74 ± 0.08 | 1.09** |

*Calculated from y = 4.4979 + 0.3441p − 0.1269q − 0.004845p*q + 0.00099qq Where p—total double bond numbers in TG; q—total carbon numbers in acyl chains of TG
**The differences between determine and calculated correction factors are over the experimental error. See text for detailed discussion.

The results demonstrated that the longer the acyl chain lengths and the lower the unsaturation index, the lower the sensitivity of TG molecular species in positive-ion ESI/S (FIG. 2 and Table 1) with only one recognized exception (i.e., T20:4 TG). The results demonstrated that there were no differences of sensitivity correction factors between TG regioisomers (Table 1). A least-square regressive nonlinear curve fitting was performed to obtain correction factors for sensitivity of TG molecular species (except for T20:4 TG) as follows:

$$y=4.4979+0.3441p-0.1269q-4.845\times10^{-3}p*q+9.9\times10^{-4}q^2, \quad [3]$$

where y is a correction factor for sensitivity effect relative to T17:1, q is the total carbon number in the three acyl chains of a TG species, and p is the double bond number in a TG species.

To further assess the impact of arachidonoyl-containing triglycerides on the unanticipated lower sensitivity of T20:4 TG during ESI/MS analysis, we synthesized multiple naturally occurred arachidonyl-containing TG molecular species (i.e., 16:0/20:4/16:0, 16:0/18:1/20:4, 18:0/20:4/18:1, and 18:2/20:4/18:2 TG) and examined their ESI/MS spectroscopic properties (FIG. 1B) The experimentally determined correction factors for each of these species were generally well within the experimental error of the sensitivity factors calculated utilizing Eq. [3] (Table 1). It should be noted that the experimentally determined sensitivity factor of 18:2/20:4/18:2 TG (which contains 8 double bonds) was ~13% less than that calculated from Eq. [3]. Collectively, these results demonstrate that Eq. [3] allows accurate quantification for most naturally occurring triglycerides. However, triglycerides containing 8 to 12 double bonds are within 10-15% algorithm-predicted values and those with ≧12 double bonds should be accounted for by independent internal standards containing a similar number of double bonds. It should be recognized that the overwhelming amount of TG molecular species in biological samples contain fewer than 6 double bonds in the three acyl chains (collectively) allowing accurate quantitation using this algorithm. Moreover, direct comparisons between highly unsaturated molecular species (e.g., T20:4 TG) will still be valid, although absolute quantitative values derived from this algorithm should be interpreted with caution in the case of TG containing ≧12 double bonds.

G. Fingerprinting of TG Molecular Species Using Positive-Ion ESI Tandem Mass Spectrometry with Neutral Loss Scanning a given mass value. The peak intensity ratio of acyl chains during neutral loss scanning reflected the number of each type of acyl chain present in the mixture of TG molecular species. For example, the intensity ratio of peaks at m/z 814 and 840 was present in a ratio of 3:2 during neutral loss scanning of palmitic acid (256) (Row B in FIG. 4) consistent with the presence of three palmitates in the molecular species at m/z 814 (T16:0 TG) and two palmitates in the molecular species at m/z 840 (18:0/16:0/16:0 TG). Tabulation of individual ion abundance (absolute ion counts) from the neutral loss scanning of each individual fatty acid with the molecular mass of the TG parent ion can be used to generate a two-dimensional matrix from which the fingerprinting of TG molecular species is possible (Table 2 below).

TABLE 2

Quantitative Analysis of an Equimolar Mixture of TG Using Positive-Ion ESI/MS/MS in Neutral Loss Mode

| [M + Li]+ | TG Species | 16:0 (NL 256) | 17:1 (NL 268) | 18:1 (NL 282) | 18:0 (NL 284) | Total Ion Counts* | Total TG (nM) |
|---|---|---|---|---|---|---|---|
| 814 | T16:0 | 165.2 ± 9.9 | | | | 239.42 ± 17.6 | 9.3 ± 0.7 |
| 840 | 16:0/16:0/18:1 | 123.4 ± 4.9 | | 55.5 ± 2.4 | | 245.1 ± 12.3 | 9.5 ± 0.5 |
| 850 | T17:1 | | 258.4 ± 12.5 | | | 258.4 ± 12.5 | 10.0 ± 0.5 |
| 892 | T18:1 | | | 207.7 ± 10.1 | | 266.3 ± 10.8 | 10.3 ± 0.4 |
| 894 | 18:1/18:1/18:0 | | | 118.0 ± 7.7 | 52.1 ± 2.3 | 243.0 ± 11.5 | 9.4 ± 0.4 |
| | Total Ion Counts* | 408.5 ± 19.9 | 258.4 ± 12.5 | 510.9 ± 28.5 | 74.4 ± 3.6 | | 48.5 ± 2.5 |
| | Total FA (nM) | 47.4 ± 2.3 (5) | 30.0 ± 1.5 (3) | 59.3 ± 3.3 (6) | 8.6 ± 0.4 (1) | 145.3 ± 6.2 | |

Our aforedescribed ESI/MS/MS of TG molecular species demonstrates that a set of abundant product ions could be generated by collisional activation which corresponded to the neutral loss of each fatty acid molecular species in the selected TG peak (insets in FIG. 3). Accordingly, we examined the abundance of product ions generated from TG molecular species and determined that the total number of ion counts corresponding to each fatty acid was proportional to the number of acyl chains in the parent TG molecular species (within 10% of the experimental error). For example, product ions at m/z 632, 606, and 584 in FIG. 3A correspond to the neutral loss of palmitic acid, oleic acid, and arachidonic acid from the lithiated 16:0/18:1/20:4 TG quasimolecular ion (m/z 888) which are present in a ratio of 1:1:1 (FIG. 3A). Similarly, product ions m/z 632 and 610 (FIG. 3B) correspond to the neutral loss of oleic acid and arachidonic acid from the lithiated 18:1/20:4/18:1 TG molecular ion (m/z 914) which are present in a ratio of 2:1 reflecting their abundance in the parent TG. Therefore, we explored the possibility that positive-ion ESI tandem mass spectrometry in the neutral loss mode can provide an informative fingerprint of the TG molecular species directly from biological samples without the need for prior chromatographic separation.

First, positive-ion ESI tandem mass spectra of an equimolar mixture of T:16:0, 18:1/16:0/16:0, T17:1, T18:1, and 18:1/18:1/18:0 TG (10 nM for each component) were acquired by scanning for the neutral loss of 256, 268, 282, and 284 [corresponding to the neutral loss of palmitic acid, heptadec-10-enoic acid (17:1), oleic acid, and stearic acid, respectively] (FIG. 4). Arrangement of sequential neutral loss spectra of individual fatty acids in conjunction with their parent ion peaks results in the generation of a 2D spectrum which provides a detailed fingerprint of each of the acyl constituents contained in all the isobaric parent ions at With a known concentration of internal standard, this 2D mass spectroscopic procedure can directly quantitate the molecular species distribution of TG from chloroform extracts of biological samples as described below.

From the two-dimensional matrix composed of absolute ion counts generated from the neutral loss scanning of individual fatty acids, the relative contribution of individual isobaric molecular species of TG to each parent ion peak can be quantitated. After the generation of the parent ion, all fatty acids examined (i.e., 16:0, 17:1, 18:0, 18:1, 18:2, and 20:4) derived from the parent ion were released with equal efficiency after collisional activation under the conditions employed (FIG. 3). Accordingly, individual molecular species contributions can be calculated from the relative ion counts present at each molecular mass by identifying a molecular species which has a single fatty acid represented. This unitary response factor can then be utilized to deconvolute molecular species information from the 2D matrix of ion counts and TG molecular species mass. This approach does not determine the regiospecificity of each fatty acid in the glycerol backbone but does allow the quantification of the three fatty acids which reside on the glycerol of each TG molecular species. For example, the molecular species at m/z 840 appeared in neutral loss scanning mass spectra of palmitic acid (16:0, MW 256) and oleic acid (18:1, MW 282) with an approximate ratio of 2:1 (Rows B and D in FIG. 4; Table 2), suggesting that this molecular species contains two palmitates and one oleate. The total ion counts of this molecular species (after correction for $^{13}C$ isotope effects and sensitivity effects) were almost identical with the internal standard (i.e., T17:1 TG; Table 2). The obtained concentration of each individual molecular species was identical within experimental errors (right column in Table 2; 10 nM).

H. Quantitation of TG Molecular Species in Lipid Extracts of Rat Myocardium by Positive-Ion ESI Tandem Mass Spectrometry in the Neutral Loss Mode As previously reported, positive-ion ESI mass spectra of lipid extracts from rat myocardium demonstrated predominant lithiated choline-containing phospholipids (e.g., m/z 765, 767, 789, 793, and 817) as well as lithiated TG molecular species (e.g., m/z 814 and 840). Since most biological tissues have substantially more choline-containing phospholipids than TG, this overlap effectively precludes the direct quantitation of TG molecular species. However, application of positive-ion ESI tandem mass spectrometry in the neutral loss mode facilitates their quantitative analysis by "spectroscopic" resolution since the neutral loss of fatty acids is absent in choline glycerophospholipids due to the >100-fold more rapid loss of the polar head group than the fatty acid after collisional activation (27).

We recognized that by scanning all potential naturally occurring fatty acids of lipid extracts from rat myocardium, a two-dimensional matrix (one dimension corresponding to the fatty acids occurring in the TG molecular species of lipid mixtures and a second corresponding to parent molecular ions) could be constructed which would reveal a detailed fingerprint of individual TG molecular species directly from lipid extracts (FIG. 5). We and others have previously demonstrated that the predominant naturally occurring fatty acids in TG molecular species are 16:0, 16:1, 18:1, 18:2, and 20:4 (FIG. 5). In chloroform extracts of rat myocardium, there were more than 10 major crosspeaks present at m/z 812, 814, 836, 838, 840, 862, 864, 866, 888, 890, 892, 912, and 914 as well as an intense peak corresponding to internal standard (m/z 850) which was omitted for clarity in FIG. 5. Positive-ion ESI tandem mass spectra with NL of palmitoleic acid (16:1) and palmitic acid demonstrated several abundant buried TG molecular ion peaks (e.g., m/z 810 and 812 in Row B and m/z 812, 814, and 840 in Row C, FIG. 5).

By recording the cross-peak ion abundance of all relevant molecular ions (>1 mol % of total TG content) in the 2D spectrum by correcting the directly measured ion intensity for $^{13}$C isotope effects, a 2D matrix was obtained (Table 3). From each molecular ion in the 2D mass spectrum, the total carbon number and total number of double bonds collectively present in the three aliphatic chains can be calculated and defined as q:p (listed in parentheses in the second column in Table 3), where q is the total carbon number and p is the double bond number in the three acyl chains of the TG species. To deconvolute the molecular species information in Table 2, an iterative procedure must be employed.

First, the lowest abundant neutral loss ion in a row is located and for that molecular species the other two acyl chains ($m_2$:$n_2$ and $m_3$:$n_3$ must obey $$m_2 + m_3 = q - m \quad [4]$$

and $$n_2 + n_3 = p - n_1, \quad [5]$$

where $m_1$, $m_2$, and $m_3$ are integers which represent total carbon number and $n_1$, $n_2$, and $n_3$ represent total double bonds in three acyl chains, respectively. Since fatty acids in isobaric molecular species of TG must contain reciprocal changes in the carbon numbers and the number of double

TABLE 3

Tandem ESI Mass Spectrometric Analyses of TG Molecular Species in Lipid Extracts of Rat Myocardium (pmol/mg of protein)

| m/z | Major Molecular Species | NL16:1 | NL16:0 | NL17:1 | NL18:2 | NL18:1 | NL18:0 | NL20:4 | Total Ion Counts* | TG Content |
|---|---|---|---|---|---|---|---|---|---|---|
| 810 | 16:0/16:1/16:1 (48:2) | 10.5 ± 1.8 | 4.9 ± 6.6 | | | | | | 16.9 ± 2.6 | 15 ± 2 |
| 812 | 16:0/16:0/16:1 (48:1) | 17.4 ± 1.5 | 35.5 ± 3.2 | | | | | | 66.2 ± 4.1 | 59 ± 5 |
| 814 | T16:0(48:0) | | 43.4 ± 2.2 | | | | | | 62.9 ± 2.6 | 56 ± 4 |
| 836 | 16:1/16:1/18:1 (50:3) | 39.4 ± 2.9 | | | | 22.2 ± 1.2 | | | 66.2 ± 4.1 | 59 ± 4 |
| 838 | 16:0/16:1/18:1 & (50:2) | 33.6 ± 2.2 | 66.7 ± 4.7 | | 9.8 ± 0.8 | 33.3 ± 2.5 | | | 172.7 ± 12.1 | 155 ± 13 |
| 840 | 16:0/16:0/18:1 (50:1) | | 47.5 ± 1.1 | | | 25.2 ± 1.0 | | | 102.7 ± 2.3 | 92 ± 5 |
| 850 | T17:1(53:3) | | | 167.6 ± 8.7 | | | | | 167.6 ± 8.7 | [150] |
| 862 | 16:1/18:1/18:2 & (52:4) | 32.5 ± 2.6 | 33.3 ± 2.2 | | 95.0 ± 7.2 | 33.9 ± 2.0 | | 3.3 ± 0.2 | 210.0 ± 10.2 | 189 ± 12 |
| 864 | 16:0/18:1/18:2 & (52:3) | 13.5 ± 1.5 | 46.4 ± 3.8 | | 55.2 ± 5.6 | 76.0 ± 7.2 | | | 221.3 ± 17.6 | 198 ± 16 |
| 866 | 16:0/18:1/18:1 (52:2) | | 26.9 ± 2.2 | | | 53.8 ± 3.1 | | | 106.1 ± 5.1 | 95 ± 7 |
| 888 | 18:1/18:2/18:2 & (54:5) | | 9.7 ± 0.4 | | 118.6 ± 6.7 | 52.3 ± 3.1 | | 10.4 ± 0.6 | 203.2 ± 18.7 | 182 ± 17 |
| 890 | 18:1/18:1/18:2 (54:4) | | | | 54.3 ± 3.6 | 100.4 ± 6.6 | | 2.3 ± 0.2 | 182.6 ± 9.9 | 163 ± 11 |
| 892 | T18:1(54:3) | | | | | 67.2 ± 6.7 | | | 83.0 ± 7.4 | 74 ± 7 |
| 894 | 18:0/18:1/18:1 (54:2) | | | | 6.1 ± 0.7 | | 10.0 ± 0.8 | | 23.0 ± 1.2 | 21 ± 1 |
| 912 | 18:1/18:2/20:4 (56:7) | | | | 21.7 ± 1.5 | 17.8 ± 1.4 | | 19.5 ± 1.6 | 54.5 ± 3.2 | 49.0 ± 4 |
| 914 | 18:1/18:1/20:4 & (56:6) | | | | 14.5 ± 1.2 | 6.2 ± 0.5 | 14.1 ± 1.2 | 15.8 ± 1.4 | 59.0 ± 4.2 | 53 ± 4 |
| | Total Ion Counts* | 166.6 ± 14.1 | 394.2 ± 31.5 | 167.6 ± 8.7 | 412.9 ± 33.8 | 577.8 ± 43.0 | 29.4 ± 1.8 | 53.5 ± 3.8 | | 1460 ± 115 |
| | FA Content | 447 ± 41 | 1058 ± 94 | [450] | 1109 ± 91 | 1551 ± 136 | 79 ± 5 | 144 ± 10 | 4388 ± 368 | | bonds, these two acyl chains can be readily defined from ion peaks corresponding to the neutral loss of fatty acids in the same row of Table 3.

Next, the lowest abundant peak is subtracted from the acyl chains in $m_2$, and $m_3$.

After subtraction, the next lowest abundant ion is located and a second round of deconvolution can be performed to identify a second isobaric molecular species. All TG molecular species can be defined by repeated iteration of this procedure. For example, in the TG molecular species present at m/z 862 (i.e., 52:4), there are five cross-peaks present in the same row of Table 3 resulting from the neutral loss of 16:0, 16:1, 18:1, 18:2, and 20:4. The lowest abundant ion present from the neutral loss of 20:4 ($3.3 \times 10^3$ ion counts) is utilized for the first round of deconvolution. The other two acyl chains must contain 32 carbons and no units of unsaturation, which is only possible with two 16:0 chains. Thus, the molecular species is 16:0/16:0/20:4 TG which represents $3.3 \times 10^3$ ion counts relative to the internal standard. By subtracting the contribution of 16:0/16:0/20:4 TG molecular species from the ion abundance of NL 16:0 in the same row, a new value is obtained which is utilized to begin the second round of deconvolution. The next lowest abundant ion is located at the cross-position reflecting NL of 16:0 with $26.7 \times 10^9$ ion counts [$(33.3-6.6) \times 10^3$]. Thus, the other two acyl chains must contain 36 carbons with 4 units of unsaturation which can successfully be fit by two 18:2 chains. Therefore, the molecular species responsible for these peaks is 16:0/18:2/18:2 TG with $\sim 27 \times 10^3$ ion counts relative to the internal standard. The remaining ions in the m/z 862 row are present in an approximate 1:1:1 ratio corresponding to a 16:1/18:1/18:2 TG. Therefore, the molecular ion at m/z 862 can be deconvoluted into parts composed of 16:0/16:0/20:4, 16:0/18:2/18:2, and 16:1/18:1/18:2 TG molecular species with an approximate ratio of 1:9:10. All other molecular ions are similarly deconvoluted and the major molecular species corresponding to each molecular ion are listed in the second column of the 2D matrix (Table 3).

Our example demonstrates that TG content and molecular species composition are directly quantified from chloroform extracts of biological samples. By employing correction factors necessary to accommodate the differential sensitivity of individual TG molecular species for ionization (relative to an internal standard (T17:1 TG)), TG content can be quantified by positive-ion ESI mass spectrometry over a three order of magnitude concentration range with less than 10% error. Moreover, by generating a 2D matrix comprised of axes corresponding to parent ions and the neutral loss of fatty acid, the methodology described herein can be used to deconvolute the TG molecular species overlapping with other polar lipids as well as calculate contributions of individual isobaric molecular species to each parent ion peak. Thus, ESI/MS/MS in conjunction with appropriate matrix analysis allows a detailed molecular species fingerprint of individual TG molecular species directly from chloroform extracts of biological samples.

In an aspect, the term "matrix analysis' includes data deconvolution and optionally data normalization.

The aforerecited expression 1-5 represent equations or algorithms which in an aspect we applied to provide a TG molecular species determination.

There are some inherent limitations present in this inventive methodology. First, the regiospecificity of acyl chains and the location of double bonds in individual acyl chains can not be defined by this method. Second, correction factors derived from the algorithm generated herein are only accurate to ±5% for molecular species containing less than 8 double bonds (collectively) and only accurate to ±15% for molecular species containing 8 to 12 double bonds (collectively). Fortunately, highly polyunsaturated TG molecular species (>8 double bonds, collectively) are rare in biological samples. If an accurate analysis of TG molecular species containing multiple polyunsaturated fatty acyl chains is required, use of additional internal standards with a similar degree of unsaturation would be prudent. Third, both the collisional activation energy as well as spectrometer tuning and calibration are of substantial importance in generating a 2D matrix which accurately reflect TG molecular species content in the neutral loss mode. If the collisional activation energy is too high (e.g., >40 eV), fragmentation of acyl chains becomes severe and the abundance of product ions corresponding to neutral loss of fatty acids from a TG molecular species will be compromised by the further differential fragmentation of these product ions. If the collisional activation energy is too low (e.g., <30 eV), the efficiency of collisional dissociation is lost and the exquisite sensitivity of this method is compromised. Therefore, this dc offset voltage set on the second quadrupole must be tested initially on each instrument. Moreover, the tuning and calibration of the spectrometer are also critical since the accuracy of this methodology is not only dependent upon the mass accuracy of both the first and third quadrupoles but also dependent upon the neutral loss mass difference between these two analyzers. Finally, fluctuations of experimental conditions (e.g., infusion rate, drying gas temperature and pressure, collisional gas pressure and energy, and vacuum system) during neutral loss scanning must be avoided. Averaging several sets of acquired experimental data at different time periods from an identical sample can minimize this type of experimental error.

Aside from the aforegoing limitations, 2D mass spectrometry of TG molecular species is a new, rapid, and convenient and direct approach to analyze the TG content of biological samples under different pathophysiologic perturbations. Although minor errors (typically less than 10%) are inherent in the assumptions utilized, fingerprinting of TG molecular species in disease states by the methods described herein provides the most discriminating comparisons between TG molecular species described to date. Furthermore, through the utilization of isotopically labeled fatty acids (e.g., deuterium or 13C) and giving these to subjects or patients unique insights into the turnover of individual molecular species are possible which will hopefully lead to an increased understanding of the role of TG in health and disease.

In an aspect, the above-described inventive methods are utilized by physicians and pharmaceutical companies to determine the risk of each individual (or group of) molecular species as an independent factor in the development of coronary artery disease, stroke, atherosclerosis and obesity as well as to target agents to selectively modify triglyceride molecular species (e.g., saturated triglycerides). Coronary artery disease, stroke, atherosclerosis and obesity are afflictions of humans which take hundreds of thousands of lives each year unnecessarily. Medical advances which assess the risk of an individual to develop one or more of these afflictions are highly desired. Moreover, these methods can be utilized to determine which lipid lowering drug is most efficacious in clinical trials and to monitor the response of patients to tailored drug therapy.

In an aspect these inventive methods are utilized to determine and identify a lipid lowering drug(s) which is most efficacious in clinical trials and other tests and to monitor the response of patients to tailored drug therapy.

Lipid lowering drugs are especially useful for treating patients who have high levels of fat in the blood which may have come about as a result of an inherited condition known as familial hyperlipidaemia. Such lipid lowering drug therapy is highly desired to lower the levels of fat in the blood and to lower the risk of atherosclerosis (hardening of the arteries) and heart disease, and an early death. From vast libraries of potential candidate drugs for pharmacological effective treatment, the management of such libraries need to have better ways of assessing and identifying those candidate drugs which have the highest potential to provide patient lipid lowering capability in practice. In an aspect, this invention provides a method of identifying those lipid lowering drugs which have the capability to lower lipid concentrations in the blood streams of humans after the administration of an effective amount of a lipid lowering drug to that patient.

Lipid lowering drugs are useful in treating coronary artery disease which is the number one killer of Americans today. This disease is caused by the buildup on plaque, deposits of fatty like substances and is called atherosclerosis. When a coronary artery is blocked by such plaque a heart attack can occur which is termed a myocardial infarction. It is highly desired to identify a lipid lowering drug and to assign a risk to an individual of a potential development of a medical problem due to high fat levels in his/her blood.

Recently there have been strides in pharmacogenomics which relates to the tailoring of drugs for individuals based on individual genomic characteristics that may play an important part in the individual's response to a drug. Individual drug therapy is likely to become a major therapy in the fight against killer diseases. Treating physicians benefit by knowing whether a drug efficacy is subject to genetic polymorphisms in the patient being treated which inhibit the patients response to the drug treatment. Feedback to the treating physician on the drug's biochemical response within the treated subject is of great importance in determining better how to use the drug in a more effective individual specific therapy.

In an aspect, the methods herein are useful to indicate the risk or likelihood of getting a disease, help confirm a diagnosis and assist in planning or customizing patent treatment. A method for assessing and assigning a risk to each individual (or group of individuals) based on TG molecular species as an independent factor in the development of at least one of condition in that individual for a medical condition selected from coronary artery disease, stroke, atherosclerosis and obesity comprises analyzing a biological sample of an individual for TG molecular species determination, administering a therapeutic amount of a drug to the individual, analyzing a corresponding biological sample of said administered individual, comparing the TG molecular species determination after drug administration with the TG molecular species determination prior to the drug administration and determining a risk therefrom associated with that individual.

The comparison of the TG molecular species determination of the biological samples is indicative of development of the condition for that individual. A risk is assigned to that individual for a respective medical condition which is indicative of the risk to that individual developing that respective medical condition at some time during his/her lifetime.

A method for determining an agent which selectively targets triglyceride molecular species (e.g., saturated triglycerides) comprises analyzing a biological sample of at least one individual for TG molecular species determination, administering a therapeutic amount of a drug to the individual, analyzing a biological sample of said administered individual, comparing the TG molecular species determination after said administration with the TG molecular species determination prior to the drug administration and determining an effect if any on the individual of the drug administration. In an aspect, the comparison of the TG molecular species determination of the biological samples is indicative of development or risk of the condition for that individual.

A method of identifying a candidate lipid modulating drug having lipid modulating drug efficacy comprises selecting a biological sample to be taken, analyzing a biological sample of at least one individual for TG molecular species determination, administering a candidate lipid lowering drug to the individual, analyzing a biological sample of said administered individual, comparing the TG molecular species determination after said administration with the TG molecular species determination prior to the drug administration and determining an effect if any on the individual of the drug administration. In an aspect, the comparison of TG analysis is indicative of the lipid metabolic altering capacity of an administered drug. In an aspect, the amount of candidate lipid lowering drug provided to the individual is a therapeutic amount and the drug is a pharmacologically acceptable chemical.

In an aspect, dynamic incorporation of stable isotopes $^2$H palmitate and oral administration the timed dynamic response to lipid loading and turnover can be assessed.

In an aspect, a method to diagnose and determine the response of patients to tailored drug therapy comprises analyzing a biological sample of at least one individual for TG molecular species determination, administering a therapeutic amount of a drug to the patient, analyzing a biological sample of said administered to patient, comparing the TG molecular species determination after the administration with the TG molecular species determination prior to the drug administration and determining an effect if any on the individual of the drug administration. In an aspect, the comparison of TG analysis is indicative of a tailored drug therapy. In an aspect, the amount of drug provided to the individual is a therapeutic amount and the drug is a pharmacologically acceptable chemical.

In an aspect a method of screening candidate chemicals for lipid modulating potential in a subject comprises analyzing a biological sample of at least one individual for TG molecular species determination, administering a drug to that biological subject, analyzing a biological sample taken from the treated subject, comparing the TG molecular species determination of the treated subject with a TG molecular species determination prior to the drug administration and determining therefrom an effect on the subject of the drug administration. In an aspect, the comparison of TG analysis is indicative of a candidate chemical having a lipid modulating potential. In an aspect, the amount of candidate lipid lowering drug provided to the individual is a therapeutic amount and the drug is a pharmacologically acceptable chemical.

All publications, patents and patent applications are herein incorporated by reference in their entirety to the same extent as if each individual publication, patent or patent application was specifically and individually indicated to be incorporated by reference in its entirety.

While the present invention has been described with reference to what are presently considered to be the preferred examples, it is to be understood that the invention is not limited to the examples herein. Rather the scope of the invention is intended to cover various modifications and equivalent arrangements included within the spirit and scope of the appended claims.

ACKNOWLEDGMENTS

References

1. Saudek, C. D., and Eder, H. A. (1979) Lipid metabolism in diabetes mellitus. Am. J. Med. 66, 843-852.
2. Dhalla, M. S., Elimban, V., and Rupp, H. (1992) Paradoxical role of lipid metabolism in heart function and dysfunction. Mol. Cell. Biochem. 116, 3-9.
3. Lee, Y., Hirose, H., Ohneda, M., Johnson, J. H. McGarry, J. D., and Unger, R. H. (1994) β-cell lipotoxicity in the pathogenesis of non-insulin-dependent diabetes mellitus of obese rats: Impairment in adipocyte β-cell relationships. Proc. Natl. Acad. Sci. USA 91, 10878-10882.
4. Unger, R. H. (1995) Lipotoxicity in the pathogenesis of obesity-dependent NIDDM. Diabetes 44, 863-870.
5. Goldberg, I. J. (1996) Lipoprotein lipase and lipolysis: Central roles in lipoprotein metabolism and atherogenesis. J. Lipid Res. 37, 693-707.
6. Lopaschuk, G. D. (1996) Abnormal mechanical function in diabetes: Relationship to altered myocardial carbohydrate/lipid metabolism. Coron. Artery Dis. 7, 116-128.
7. Stanley, W. C., Lopaschuk, G. D., and McCormack, J. G. (1997) Regulation of energy substrate metabolism in the diabetic heart. Cardiovasc. Res. 34, 25-33.
8. Han, X., Abendschein, D. R. Kelley, J. G., and Gross, R. W. (2000) Diabetes-induced changes in specific lipid molecular species in rat myocardium. Biochem. J. 352, 79-89.
9. Innis, S. M. (1993) The colostrum-deprived piglet as a model for study of infant lipid nutrition. J. Nutr. 123, 386-390.
10. Cole, T. G., Klotzsch, S. G., and McNamara, J. R. (1994) Measurement of triacylglyceride concentration. In Laboratory Measurement of Lipids, Lipoproteins and Apolipoproteins (Rifai, N., and Warnick, R., Eds.), pp. 81-90, AACC Press, Washington, D.C.
11. Dobson, G., Christie, W. W., and Nikolova-Damyanova, B. (1995) Silver ion chromatography of lipids and fatty acids. J. Chromatogr. B. 671, 197-222.
12. Bartle, K. D., and Clifford, A. A. (1994) Supercritical fluid extraction and chromatography of lipid materials. In Developments in the Analysis of Lipids (Tyman, J. H. P., and Gordon, M. H., Eds.), pp. 1-41, Royal Soc. Chem., Cambridge, UK.
13. Demirbuker, M., Blomberg, L., Olsson, N. U., Bergqvist, M., Herslof, B. G., and Jacobs, F. A. (1992) Characterization of triacylglycerols in the seeds of *Aquilegia vulgaris* by chromatographic and mass spectrometric methods. Lipids 27, 436-411.
14. Evershed, R. P. (1996) High resolution triacylglycerol mixture analysis using high temperature gas chromatography mass spectrometry with a polarizable stationary phase, negative ion chemical ionization, and mass resolved chromatography. J. Am. Soc. Mass Spectrom 7, 350-361.
15. Lamberto, Z. M., and Saitta, M. (1995) Principal component analysis in fast atom bombardment-mass spectrometry of triacylglycerols in edible oils. J. Am. Oil Chem. Soc. 72, 867-871.
16. Duffin, K. L., Henion, J. D., and Shieh, J. J. (1991) Electrospray and tandem mass spectrometric characterization of acylglycerol mixtures that are dissolved in nonpolar solvents. Anal. Chem. 63, 1781-1788.
17. Cheng, C., Gross, M. L., and Pittenauer, E. (1998) Complete structural elucidation of triacylglycerols by tandem sector mass spectrometry. Anal. Chem. 70, 4417-4426.
18. Myher, J. J., Kuksis, A., Geher, K., Park, P. W., and Diersen-Schede, D. A. (1996) Stereospecific analysis of triacylglycerols rich in long-chain polyunsaturated fatty acids. Lipids 31, 207-215.
19. Byrdwell, W. C., and Emken, E. A. (1995) Analysis of triacylglycerides using atmospheric pressure chemical ionization mass spectrometry. Lipids 30, 173-175.
20. Hsu, F. F., and Turk, J. (1999) Structural characterization of triacylglycerols as lithiated adducts by electrospray ionization mass spectrometry using low-energy collisionally activated dissociation on a triple stage quadruple instrument. J. Am. Soc. Mass Spectrom 10, 587-599.
21. Asbury, G. R., Al-Saad, K., Siems, W. F., Hannan, R. M., and Hill, H. H. (1999) Analysis of triacylglycerols and whole oils by matrix-assisted laser desorption/ionization time of flight mass spectrometry. J. Am. Soc. Mass Spectrom. 10, 983-991.
22. Glenn, K. C., Shieh, J. J., and Laird, D. M. (1992) Characterization of 3T3-L1 storage lipid metabolism: Effect of somatotropin and insulin on specific pathways. Endocrinology 131, 115-1124
23. Fink, L. W., and Gross, R. W. (1984) Modulation of canine myocardial sarcolemmal membrane fluidity by amphiphilic compounds. Circ. Res. 55, 585-594
24. Bligh, E. G., an Dyer, W. J. (1959) A rapid method of total lipid extraction and purification. Can. J. Biochem. Physiol. 37, 911-917
25. Han, X., and Gross, R. W. (1994) Electrospray ionization mass spectroscopic analysis of human erythrocyte plasma membrane phospholipids. Proc. Natl. Acad. Sci. USA 91, 10635-10639
26. Han, X., Gubitosi-Klug, R., A., Collins, B. J., and Gross, R. W. (1996) Alterations in individual molecular species of human platelet phospholipids during thrombin stimulation: Electrospray ionization mass spectrometry-facilitated identification of the boundary conditions for the magnitude and selectivity of thrombin-induced platelet phospholpid hydrolysis. Biochemistry 35, 5822-5832.
27. Han., X., and Gross, R. W. (1995) Structural determination of picomole amounts of phospholipids via electrospray ionization tandem mass spectrometry. J. Am. Soc. Mass Spectrom. 6, 1202-1210

What is claimed is:

1. A method for the determination of triglyceride individual molecular species composition of matter in a biological sample comprising:
   subjecting the biological sample to lipid extraction to obtain a lipid extract;
   subjecting the lipid extract to two dimensional electrospray ionization tandem mass spectrometry (ESI/MS/MS) to generate a two dimensional plot representing molecular ions of the lipid extract on an x-axis and neutral loss scans of fatty acids of the lipid extract on a y-axis; and
   comparing peak heights for the molecular ions with that for an internal standard to identify and/or quantify the triglyceride molecular species.

2. A method in accordance with claim 1 wherein the lipid extraction is a chloroform lipid extraction.

3. A method in accordance with claim 1 wherein said biological sample includes at least one blood, serum, a tissue biopsy, feces, and urine.

4. A method in accordance with claim 1 wherein said biological sample is one of a mammalian tissue and a plant tissue.

5. A method in accordance with claim 4 wherein the mammalian tissue is human tissue.

6. A method in accordance with claim 1 further comprisin determining a fingerprint profile of a triglyceride molecular species.

7. A method in accordance with claim 6 wherein said fingerprint profile represents the individual molecular species of a triglyceride composition of matter.

8. A method for the determination of triglyceride individual molecular species composition of matter directly from a lipid extract of a biological sample comprising:
  subjecting said lipid extract to electrospray ionization tandem mass spectrometry (ESI/MS/MS) to generate a two dimensional plot of molecular ions of the lipid extract versus neutral loss scans of fatty acids of the lipid extract; and
  comparing peak heights for the molecular ions with that for an internal standard to identify and/or quantify the triglyceride molecular species.

9. A method in accordance with claim 8 wherein said lipid extract is obtained via a chloroform extraction.

10. A method in accordance with claim 8 wherein said biological sample is one of a mammalian or a plant tissue.

11. A method in accordance with claim 10 wherein said mammalian tissue is human tissue.

12. A method in accordance with claim 8 wherein the biological sample is an aqueous human fluid sample subjected to at least one of centrifugation and conventional column chromatography suitable for separation of lipoproteins to resolve triglyceride into different lipoproteins.

13. A method in accordance with claim 12 wherein the aqueous human fluid sample is selected from the group consisting of whole blood, blood serum, blood plasma, liver and urine.

14. A method in accordance with claim 13 wherein the lipid extract is obtained by extraction of said biological sample with chloroform.

15. A method in accordance with claim 8 wherein said internal standard includes a control sample of triglyceride molecular species.

16. A method in accordance with claim 8 further comprising iteratively deconvoluting and optionally normalizing the peak heights for the molecular ions.

17. A method in accordance with claim 8 further comprising deconvoluting two dimensional intercept contours of the neutral loss scans.

* * * * *